(12) United States Patent
Lisanti et al.

(10) Patent No.: US 11,559,527 B2
(45) Date of Patent: Jan. 24, 2023

(54) TARGETING MITOCHONDRIAL FISSION THROUGH MDIVI-1 DERIVATIVES

(71) Applicant: LUNELLA BIOTECH, INC., Ottawa (CA)

(72) Inventors: Michael P. Lisanti, Manchester (GB); Federica Sotgia, Manchester (GB)

(73) Assignee: LUNELLA BIOTECH, INC., Ontario (CA)

( * ) Notice: Subject to any disclaimer, the term of this patent is extended or adjusted under 35 U.S.C. 154(b) by 87 days.

(21) Appl. No.: 16/954,801

(22) PCT Filed: Dec. 18, 2018

(86) PCT No.: PCT/US2018/066247
§ 371 (c)(1),
(2) Date: Jun. 17, 2020

(87) PCT Pub. No.: WO2019/126179
PCT Pub. Date: Jun. 27, 2019

(65) Prior Publication Data
US 2021/0137925 A1 May 13, 2021

Related U.S. Application Data

(60) Provisional application No. 62/608,065, filed on Dec. 20, 2017.

(51) Int. Cl.
*A61K 31/517* (2006.01)
*A61K 47/54* (2017.01)
*A61P 35/04* (2006.01)

(52) U.S. Cl.
CPC ............ *A61K 31/517* (2013.01); *A61K 47/54* (2017.08); *A61P 35/04* (2018.01)

(58) Field of Classification Search
CPC .................................................. A61K 31/517
See application file for complete search history.

(56) References Cited

U.S. PATENT DOCUMENTS

| 2005/0038051 A1* | 2/2005 | Nunnari | C07D 498/04 |
|---|---|---|---|
| | | | 514/266.2 |
| 2012/0294956 A1 | 11/2012 | Qian et al. | |
| 2014/0371251 A1 | 12/2014 | Aberger et al. | |
| 2016/0075726 A1 | 3/2016 | Neuzil | |

FOREIGN PATENT DOCUMENTS

| WO | WO 2008/145116 | 12/2008 |
| WO | WO 2017/192679 | 11/2017 |

OTHER PUBLICATIONS

McMahon et al. (2000).*
Pinedo et al. (2000).*
Marie-Céline Frantz, et al., "Mitochondria as a target in treatment", Environ Mol Mutagen, vol. 51, No. 5, Jun. 2010, 21 pages.
International Search Report for PCT/US2018/066247 dated Mar. 25, 2019, 2 pages.
Written Opinion of the ISA for PCT/US2018/066247 dated Mar. 25, 2019, 8 pages.
International Preliminary Report on Patentability for PCT/US2018/066247 dated Apr. 28, 2020, 113 pages.
Zielonka et al., "Mitochondria-Targeted Triphenylphosphonium-Based Compounds: Syntheses, Mechanisms of Action, and Therapeutic and Diagnostic Applications", Americal Chemical Society, Chem. Rev. 2017, 117, pp. 10043-10120.
European Search Report for EP 18 89 0692 dated Jul. 13, 2021.

* cited by examiner

*Primary Examiner* — Paul V Ward
(74) *Attorney, Agent, or Firm* — Nixon & Vanderhye, P.C.

(57) ABSTRACT

Derivatives of mDIVI-1 may be used to target and eliminate cancer stem cells. Disruption in the mitochondrial dynamics balance plays a role in cancer. Proteins involved in regulating mitochondrial dynamics represent potential targets for cancer treatment. Mitochondrial fission protein DRP1 is such a target. Derivatives of mDIVI-1 inhibit DRP1, and have demonstrated inhibition of tumorsphere forming capacity, migration and stemness-related signaling in breast cancer cells. These properties result from induction of mitochondrial oxidative stress and reduction of mitochondrial metabolism in the target cancer cells. The potency of an mDIVI-1 derivative may be dramatically increased through addition of at least one membrane-targeting signal and/or a mitochondria-targeting signal.

8 Claims, 24 Drawing Sheets

1.

2.

3.

4.

5.

6.

7.

8.

9.

2-butene-1,4-bis-TPP

(A)

p-xylylene-bis-TPP

(B)

(1)

(4)

(2)

(5)

(3)

TARGETING MITOCHONDRIAL FISSION THROUGH MDIVI-1 DERIVATIVES

RELATED APPLICATIONS

This application is the U.S. national phase of International Application No. PCT/US2018/066247 filed Dec. 18, 2018 which designated the U.S. and claims priority to U.S. Provisional Patent Application No. 62/608,065 filed Dec. 20, 2017, the entire contents of each of which are hereby incorporated by reference.

FIELD

The present disclosure relates to inhibiting mitochondrial function, cell migration, and cancer stem cell (CSC) signaling, through derivatives of mDIVI-1.

BACKGROUND

Researchers have struggled to develop new anti-cancer treatments. Conventional cancer therapies (e.g. irradiation, alkylating agents such as cyclophosphamide, and anti-metabolites such as 5-Fluorouracil) have attempted to selectively detect and eradicate fast-growing cancer cells by interfering with cellular mechanisms involved in cell growth and DNA replication. Other cancer therapies have used immunotherapies that selectively bind mutant tumor antigens on fast-growing cancer cells (e.g., monoclonal antibodies). Unfortunately, tumors often recur following these therapies at the same or different site(s), indicating that not all cancer cells have been eradicated. Relapse may be due to insufficient chemotherapeutic dosage and/or emergence of cancer clones resistant to therapy. Hence, novel cancer treatment strategies are needed.

Advances in mutational analysis have allowed in-depth study of the genetic mutations that occur during cancer development. Despite having knowledge of the genomic landscape, modern oncology has had difficulty with identifying primary driver mutations across cancer subtypes. The harsh reality appears to be that each patient's tumor is unique, and a single tumor may contain multiple divergent clone cells. What is needed, then, is a new approach that emphasizes commonalities between different cancer types. Targeting the metabolic differences between tumor and normal cells holds promise as a novel cancer treatment strategy. An analysis of transcriptional profiling data from human breast cancer samples revealed more than 95 elevated mRNA transcripts associated with mitochondrial biogenesis and/or mitochondrial translation. Sotgia et al., *Cell* Cycle, 11(23):4390-4401 (2012). Additionally, more than 35 of the 95 upregulated mRNAs encode mitochondrial ribosomal proteins (MRPs). Proteomic analysis of human breast cancer stem cells likewise revealed the significant overexpression of several mitoribosomal proteins as well as other proteins associated with mitochondrial biogenesis. Lamb et al., *Oncotarget*, 5(22):11029-11037 (2014).

Mitochondria are extremely dynamic organelles in constant division, elongation and connection to each other to form tubular networks or fragmented granules in order to satisfy the requirements of the cell and adapt to the cellular microenvironment. The balance of mitochondrial fusion and fission dictates the morphology, abundance, function and spatial distribution of mitochondria, therefore influencing a plethora of mitochondrial-dependent vital biological processes such as ATP production, mitophagy, apoptosis, and calcium homeostasis. In turn, mitochondrial dynamics can be regulated by mitochondrial metabolism, respiration and oxidative stress. Thus, it is not surprising that an imbalance of fission and fusion activities has a negative impact on several pathological conditions, including cancer. Cancer cells often exhibit fragmented mitochondria, and enhanced fission or reduced fusion is often associated with cancer, although a comprehensive mechanistic understanding on how mitochondrial dynamics affects tumorigenesis is still needed.

Functional inhibition of mitochondrial biogenesis using the off-target effects of certain bacteriostatic antibiotics or OXPHOS inhibitors provides additional evidence that functional mitochondria are required for the propagation of cancer stem cells. The inventors recently showed that a mitochondrial fluorescent dye (MitoTracker) could be effectively used for the enrichment and purification of cancer stem-like cells from a heterogeneous population of living cells. Farnie et al., *Oncotarget*, 6:30272-30486 (2015). Cancer cells with the highest mitochondrial mass had the strongest functional ability to undergo anchorage-independent growth, a characteristic normally associated with metastatic potential. The 'Mito-high' cell sub-population also had the highest tumor-initiating activity in vivo, as shown using pre-clinical models. The inventors also demonstrated that several classes of non-toxic antibiotics could be used to halt cancer stem cell propagation. Lamb et al., *Oncotarget*, 6:4569-4584 (2015). Because of the conserved evolutionary similarities between aerobic bacteria and mitochondria, certain classes of antibiotics or compounds having antibiotic activity can inhibit mitochondrial protein translation as an off-target side-effect.

A master regulator of the mitochondrial fission machinery is the cytoplasmic dynamin-related protein 1 (DRP1, also known as DNM1L). During mitochondrial fission DRP1 is recruited to the mitochondria and interacts with the outer mitochondrial membrane receptors. Subsequently, DRP1 polimerizes and promotes mitochondrial constriction and fission, activities that are fueled by its GTPase activity.

SUMMARY

In view of the foregoing background, it is an object of this disclosure to describe compounds containing therapeutic agents that may be used to eradicate CSCs, and methods for targeting and eradicating CSCs. It is further an object of this disclosure to describe compositions, such as pharmaceutical compositions, and methods for treating and preventing cancer, among other indications.

The present approach may also be used to treat and/or prevent tumor recurrence, metastasis, drug resistance, and/or radiotherapy resistance. Anti-cancer treatments often fail because the tumor recurs or metastasizes, particularly after surgery. Also, drug resistance and radiotherapy resistance are common reasons for cancer treatment failure. CSC mitochondrial activity may be, at least in part, responsible for these causes of treatment failure. Embodiments of the present approach may be used in situations where conventional cancer therapies fail, and/or in conjunction with or prior to anti-cancer treatments, to prevent failure due to tumor recurrence, metastasis, chemotherapy resistance, drug resistance, and/or radiotherapy resistance.

As described herein, mDIVI-1 and its derivatives may be used to selectively eradicate CSCs, treat and/or prevent tumor recurrence, metastasis, drug resistance, and/or radiotherapy resistance. Mitochondrial division inhibitor-1 (mDIVI-1) is a small molecule that selectively and reversibly inhibits DRP1. MDIVI-1 has been shown to target DRP1 by binding and suppressing both the DRP1 self-assembly into ring-like structures around the mitochondria and its capacity to catalyze GTP hydrolysis. MDIVI-1 prompts a rapid formation of interconnected mitochondria without overtly affecting other cellular structures such as the cytoskeleton or the endoplasmic reticulum. The IC50 of mDIVI-1 ranges from 1 to 50 µM, depending on the cell type. In contrast to the cytoprotective effect in neurons and cardiovascular cells, mDIVI-1 has a cytotoxic effect in hyperproliferative cancer cells and immortalized cell lines. Indeed, high DRP1 expression or activation has been described in several malignancies, and it promotes mitochondrial fission in cancer cells, which plays an important role in their proliferation and metastatic capacity. Reversal of that mitochondrial fission via DRP1 inhibition with mDIVI-1 induces apoptosis via cytochrome-c release and cell cycle arrest by impairing the assembly of mitotic spindles and cytokinesis, consequently leading to aneuploidy.

Emerging evidence suggests that mitochondrial fusion and fission, and in particular for DRP1, have a role in regulating the proliferation and survival of cancer stem cells, which are thought to be responsible for treatment failure and metastatic dissemination. DRP1-dependent fission confers chemoresistance, as chemoresistant cancer cells are prone to form highly interconnected mitochondrial networks. MDIVI-1 treatment reverses this phenotype by re-sensitizing chemoresistant cancer cells. Moreover, high DRP1 expression and mitochondrial fragmentation contribute to maintenance of brain tumor-initiating cells, and genetic ablation of DRP1 or its pharmacological inhibition with mDIVI-1 reduces their tumorigenicity both in vitro and in vivo. DRP1-dependent fission is essential for stem cell maintenance in immortalized mammary epithelial stem-like cells. Upon asymmetric cell division, stem-like cells contain a higher abundance of newly generated mitochondria, whereas cells with more aged mitochondria grow less efficiently in anchorage-independent conditions, and are primed to differentiate. DRP1 inhibition with mDIVI-1 abolished the mitochondrial asymmetric distribution of mitochondria reducing stem-cell properties in vitro, suggesting that mitochondrial fitness regulates stemness. Inactivation of DRP1 with mDIVI-1 also impedes pluripotency reprogramming.

Emerging evidence has recently shown that CSCs are critically dependent on mitochondrial function for their successful propagation and survival. The present approach demonstrates that the pharmacological inhibition of DRP1-induced mitochondrial fission with mDIVI-1 targets breast CSC survival, via induction of mitochondrial dysfunction and repression of mitochondrial metabolism. Exposure of MCF7 breast cancer cells to mDIVI-1 transforms these cells into metabolically less active cells, with minor ATP demand. This transformation appears to occur through induction of mitochondrial reactive species. These mDIVI-1-treated metabolically-repressed MCF7 cells have reduced tumorsphere-forming capacity, decreased migration, and inhibited stemness-related signaling. MDIVI-1 is also able to decrease tumorsphere formation efficiency in melanoma and lung cancer cell lines, strongly suggesting that mDIVI-1 treatment decreases the abundance of CSC also in these cancers. Consequently, mDIVI-1 derivatives have anti-cancer efficacy, and are useful in treating cancer through selectively targeting and eradicating CSCs.

The present approach may take the form of a mitochondrial fission inhibitor 1 (mDIVI-1) derivative having the general formula:

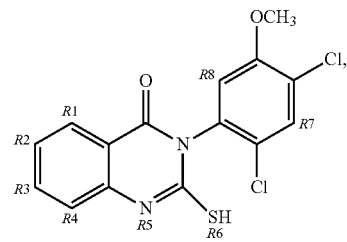

or a pharmaceutically acceptable salt thereof. Each of R1 through R8 may be selected from the group consisting of hydrogen, carbon, nitrogen, sulfur, oxygen, fluorine, chlorine, bromine, iodine, carboxyl, alkanes, cyclic alkanes, alkane-based derivatives, alkenes, cyclic alkenes, alkene-based derivatives, alkynes, alkyne-based derivative, ketones, ketone-based derivatives, aldehydes, aldehyde-based derivatives, carboxylic acids, carboxylic acid-based derivatives, ethers, ether-based derivatives, esters and ester-based derivatives, amines, amino-based derivatives, amides, amide-based derivatives, monocyclic or polycyclic arene, heteroarenes, arene-based derivatives, heteroarene-based derivatives, phenols, phenol-based derivatives, benzoic acid, benzoic acid-based derivatives, and a mitochondria-targeting signal. In some embodiments, at least one R-group is a targeting signal, such as palmitic acid, stearic acid, myristic acid, and oleic acid, a short-chain fatty acid, a medium-chain fatty acid, tri-phenyl-phosphonium (TPP), a TPP-derivative, a lipophilic cation, and 10-N-nonyl acridine orange. In some embodiments, at least one R-group is a mitochondria-targeting signal, such as one of 2-butene-1,4-bis-TPP; 2-chlorobenzyl-TPP; 3-methylbenzyl-TPP; 2,4-dichlorobenzyl-TPP; 1-naphthylmethyl-TPP; p-xylylenebis-TPP; a derivative of 2-butene-1,4-bis-TPP; a derivative of 2-chlorobenzyl-TPP; a derivative of 3-methylbenzyl-TPP; a derivative of 2,4-dichlorobenzyl-TPP; a derivative of 1-naphthylmethyl-TPP; and a derivative of p-xylylenebis-TPP.

Embodiments of an mDIVI-1 derivative may possess at least one of anti-aging activity, radiosensitizing activity, photosensitizing activity, and anti-microbial activity. In some embodiments, the mDIVI-1 derivative sensitizes cancer cells to at least one of chemotherapeutic agents, natural substances, and caloric restriction.

The present approach may also take the form of methods of treating cancer, by administering a pharmaceutically effective amount of an mDIVI-1 derivative as described herein, with a pharmaceutically acceptable carrier. Some embodiments of the present approach may take the form of methods for eradicating cancer cells, by delivering to the cancer cells a pharmaceutically effective amount of an mDIVI-1 derivative as described herein, and a pharmaceutically acceptable carrier. The targeted cancer cells may include one or more of CSCs, energetic cancer stem cells, circulating tumor cells, and treatment-resistant cancer stem cells.

Some embodiments of the present approach may take the form of methods for treating and/or preventing at least one of tumor recurrence, metastasis, drug resistance, and radiotherapy resistance. A pharmaceutically effective amount of at least one mDIVI-1 derivative as described herein may be administered. It should be appreciated that the compound may be administered prior to a cancer treatment, with a cancer treatment, following a cancer treatment, or combinations thereof.

In some embodiments, the present approach may take the form of methods for increasing the potency of mDIVI-1, through forming an mDIVI-1 derivative by chemically modifying mDIVI-1 with at least one targeting compound. For example, the targeting compound can be at least one of palmitic acid, stearic acid, myristic acid, oleic acid, a short-chain fatty acid, a medium-chain fatty acid, a lipophilic cation, tri-phenyl-phosphonium (TPP), a TPP-derivative, and 10-N-nonyl acridine orange.

DESCRIPTION

Figure 1:
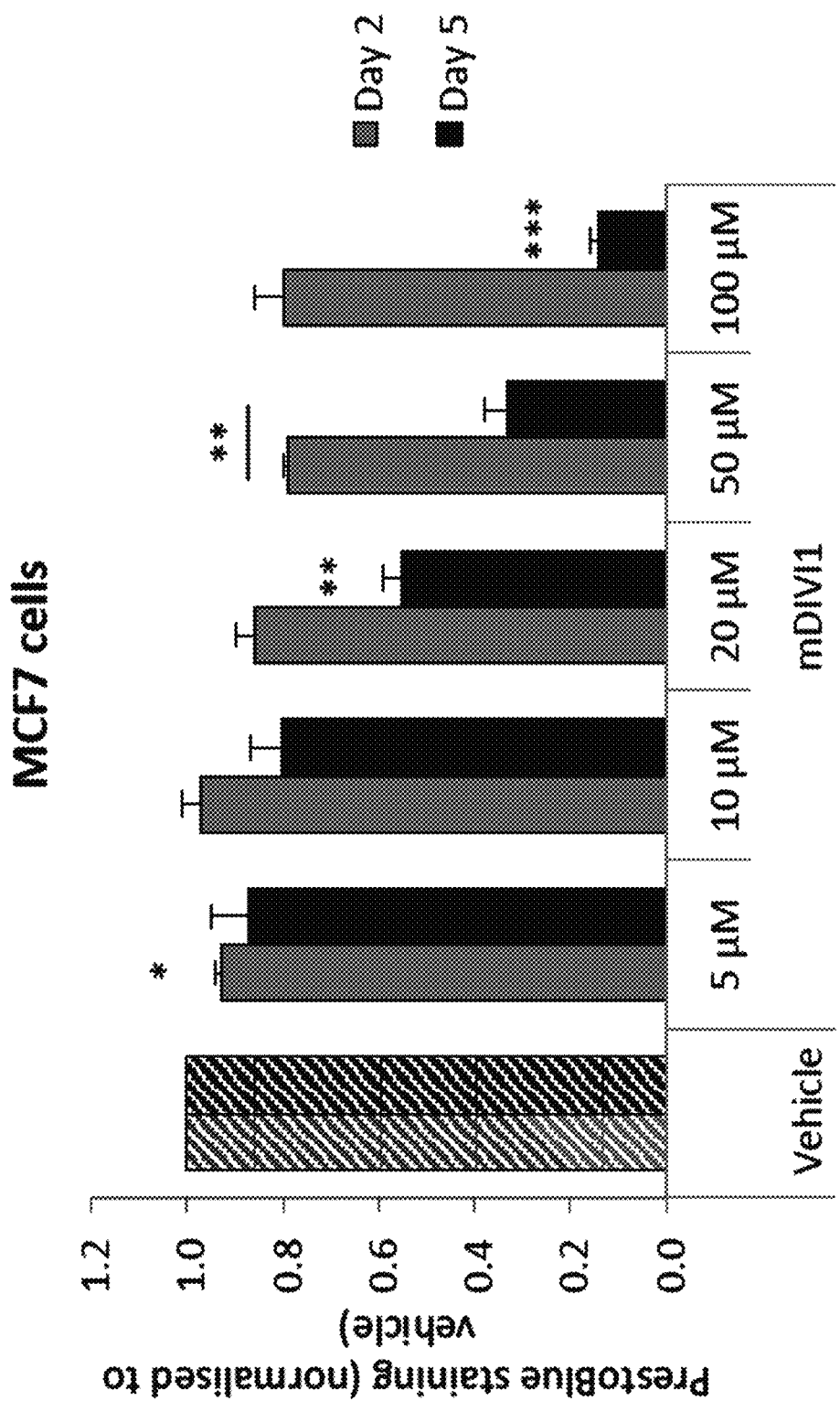
FIG. 1 shows data relating to DRP1 inhibition by mDIVI-1 treatment.

The following description illustrates embodiments of the present approach in sufficient detail to enable practice of the present approach. Although the present approach is described with reference to these specific embodiments, it should be appreciated that the present approach can be embodied in different forms, and this description should not be construed as limiting any appended claims to the specific embodiments set forth herein. Rather, these embodiments are provided so that this disclosure will be thorough and complete, and will fully convey the scope of the present approach to those skilled in the art.

The mitochondria is an untapped gateway for treating a number of afflictions, ranging from cancer to bacterial and fungal infections to aging. Functional mitochondria are required for the propagation of cancer stem cells. Inhibiting mitochondrial biogenesis and metabolism in cancer cells impedes the propagation of those cells. Inhibiting DRP1-induced mitochondrial fission with mDIVI-1 and its derivatives therefore presents an effective anti-cancer solution, as the therapeutic agent preferentially targets CSCs, reducing tumorsphere-forming capacity, decreasing cell migration, and inhibiting stemness-related signaling.

Chemical compound 3-(2,4-Dichloro-5-methoxyphenyl)-2-sulfanyl-4(3H)-quinazolinone (CAS Number 338967-87-6), synonymous with 3-(2,4-Dichloro-5-methoxyphenyl)-2,3-dihydro-2-thioxo-4(1H)-quinazolinone, and known as mDIVI-1, is a cell-permeable selective inhibitor of mitochondrial division DRP (dynamin-related GTPase) and inhibitor of the mitochondrial division dynamin (Dnm1). Mitochondrial fusion and division play important roles in the regulation of apoptosis. The structure of mDIVI-1 is shown below.

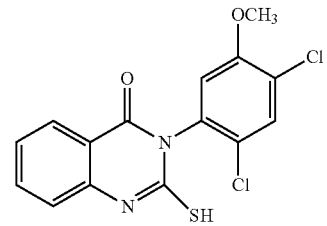 [SMILES: COc1cc(-n2c(S)nc3ccccc3c2=O)c(Cl)cc1Cl]

Numerous derivatives of mDIVI-1 have similar, if not improved, properties. Those derivatives are many in number, and in lieu of describing each mDIVI-1 derivative, the structure below identifies the locations for functional groupings. The genus of mDIVI-1 derivatives may be described as:

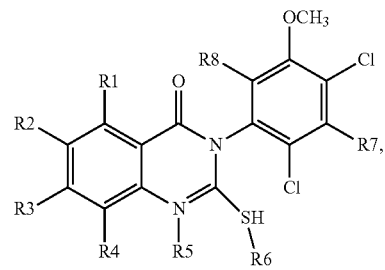

wherein each of R1 through R8 may be the same or different, and is selected from the group consisting of hydrogen, carbon, nitrogen, sulfur, oxygen, fluorine, chlorine, bromine, iodine, carboxyl, alkanes, cyclic alkanes, alkane-based derivatives, alkenes, cyclic alkenes, alkene-based derivatives, alkynes, alkyne-based derivative, ketones, ketone-based derivatives, aldehydes, aldehyde-based derivatives, carboxylic acids, carboxylic acid-based derivatives, ethers, ether-based derivatives, esters and ester-based derivatives, amines, amino-based derivatives, amides, amide-based derivatives, monocyclic or polycyclic arene, heteroarenes, arene-based derivatives, heteroarene-based derivatives, phenols, phenol-based derivatives, benzoic acid, benzoic acid-based derivatives, and one or more mitochondria-targeting signals. Notwithstanding the foregoing, it should be appreciated that R5 and R6 are optional R groups, as those groups may be absent from some embodiments depending on the oxidation state of the nitrogen or sulfur. For example, R6 will not be present if the sulfur is part of a thiol. Membrane-targeting signals include fatty acid membrane-targeting signals, such as such as palmitate, stearate, myristate, and oleate. Short-chain fatty acids, i.e., fatty acids with less than six carbon atoms, may also be used as a membrane-targeting signal. Examples of short-chain fatty acids include formic acid, acetic acid, propionic acid, butyric acid, isobutyric acid, valeric acid, and isovaleric acid. The membrane-targeting signal may also be one or more medium-chain fatty acids, having 6-12 carbon atoms.

Figure 11A:
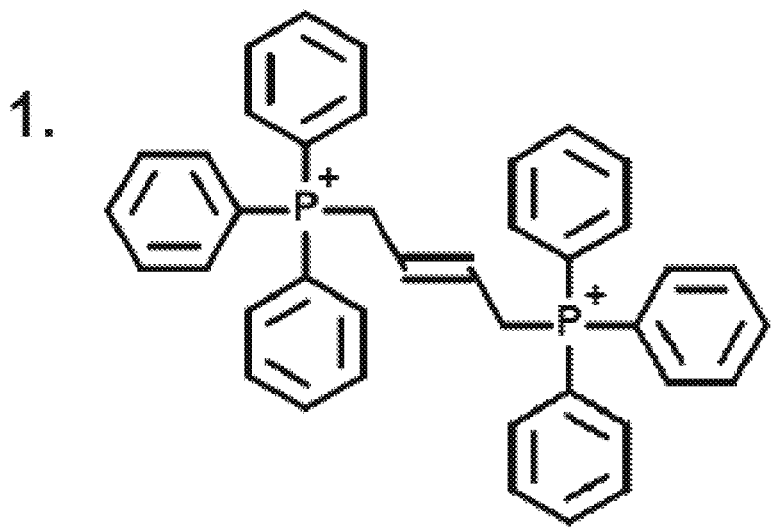
FIGS. 11A-11C show demonstrative TPP-derivative compounds.
Figure 11A:
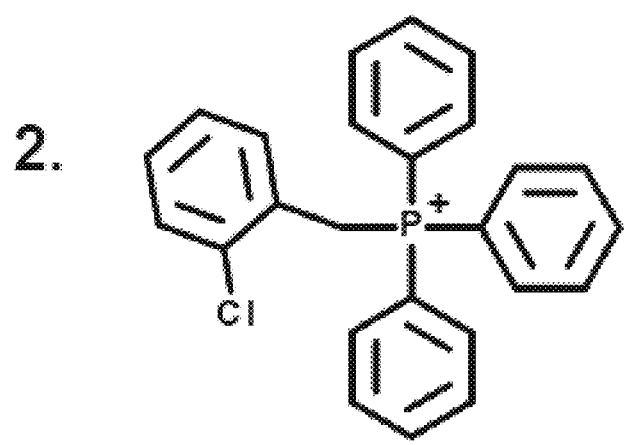
Figure 11A:
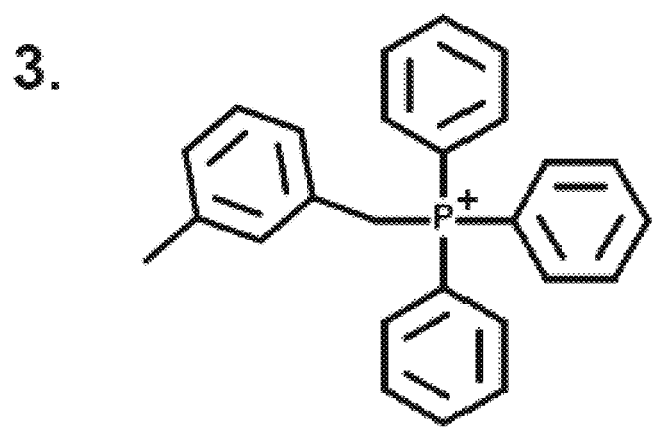
Figure 11B:
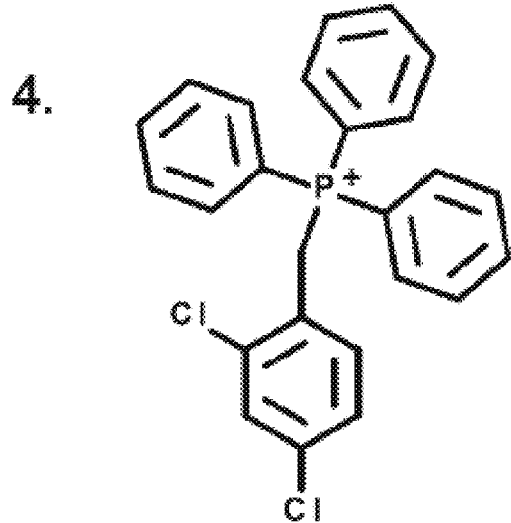
Figure 11B:
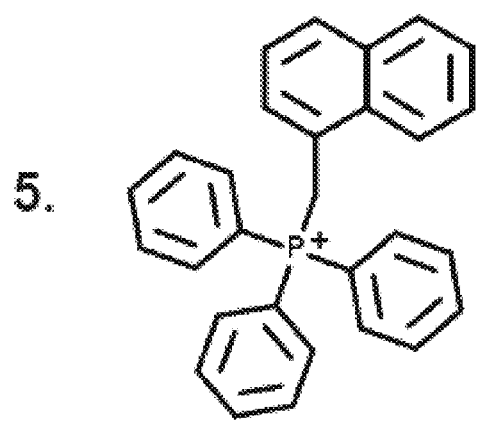
Figure 11B:
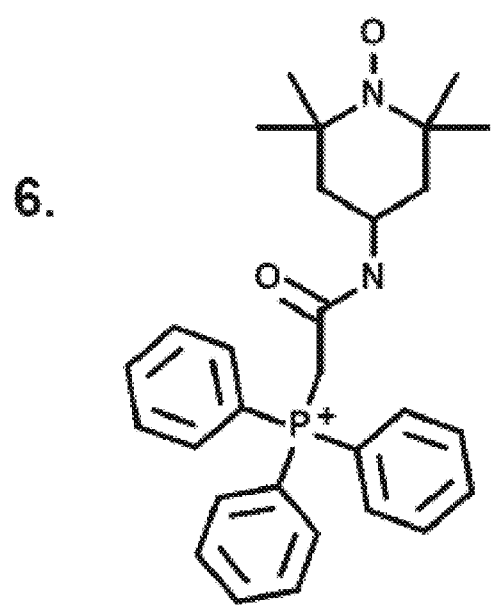
Figure 11C:
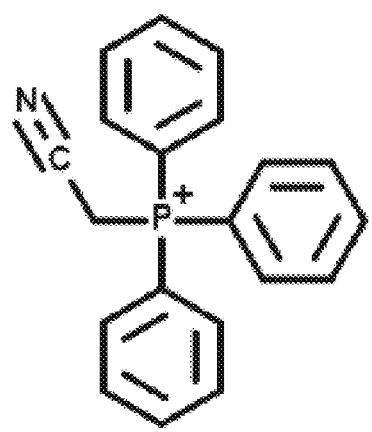
Figure 11C:
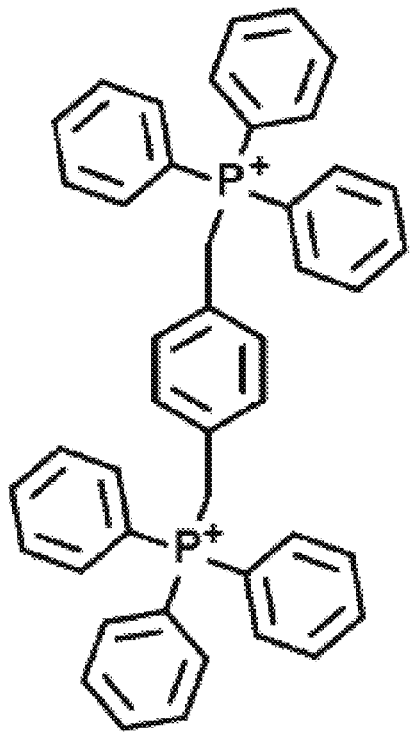
Figure 11C:
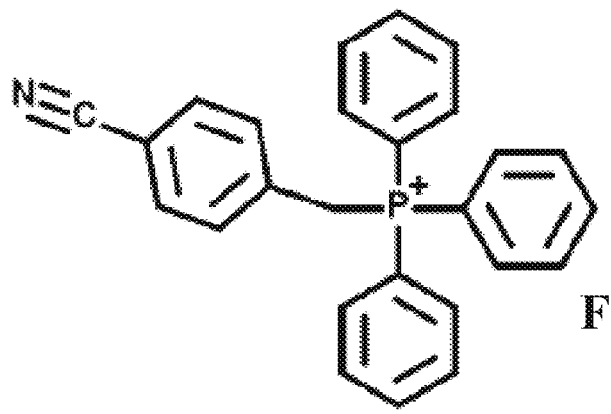
Figure 12A:
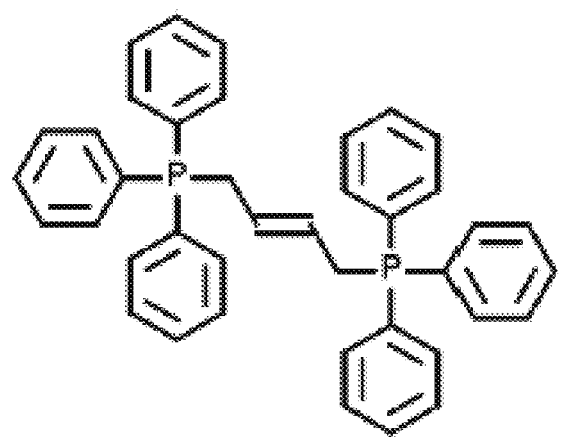
FIG. 12A shows (A) 2-butene-1,4-bis-TPP and (B) p-xylylene-bis-TPP.
Figure 12A:
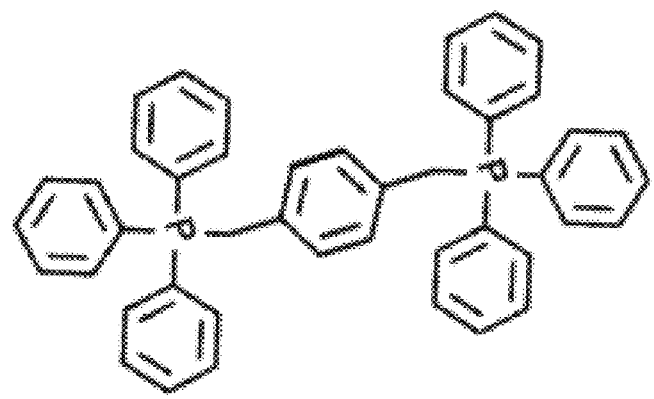
Figure 12B:
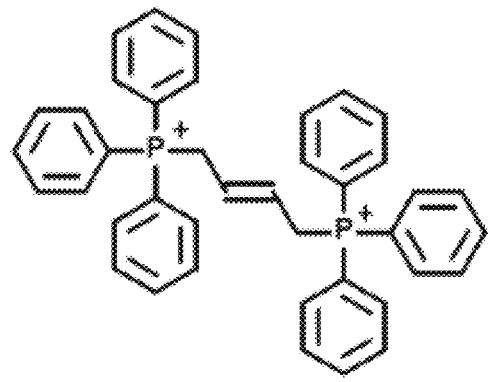
FIG. 12B shows examples of TPP-derivative compounds.
Figure 12B:
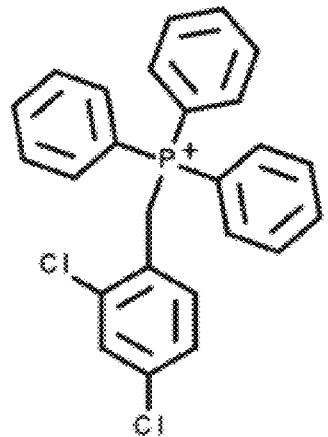
Figure 12B:
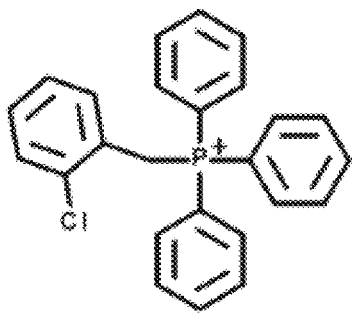
Figure 12B:
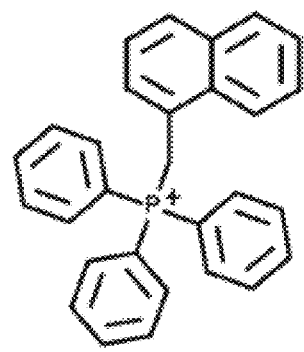
Figure 12B:
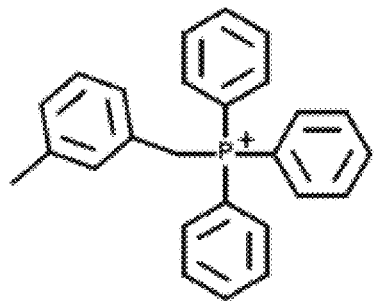
Figure 13:
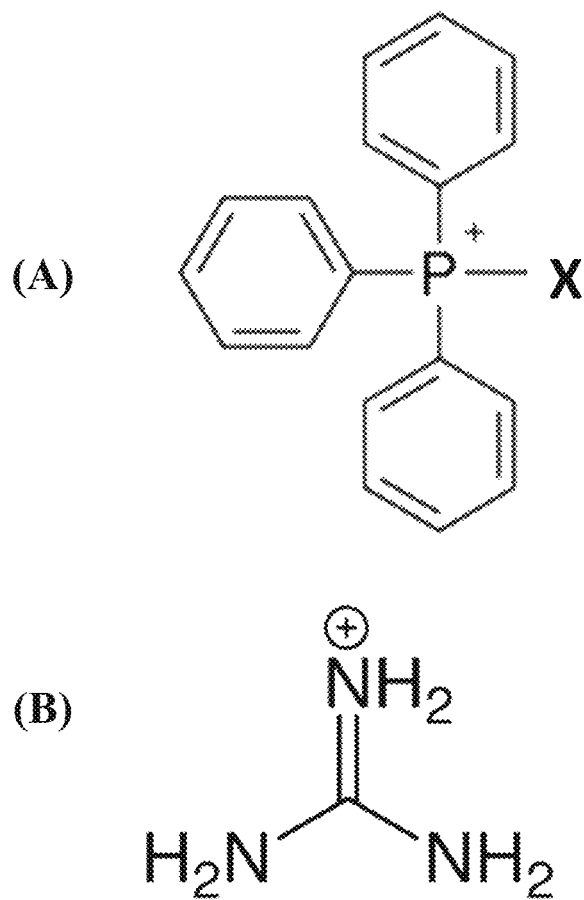
FIG. 13 shows (A) tri-phenyl-phosphonium (TPP) and (B) guanidinium.

A mitochondria-targeting signal may increase the agent's potency by over 100 times or more, and in some instances of 1000 times, such that an mDIVI-1 derivative with a targeting signal requires significantly less amount to achieve a therapeutic outcome than the same compound without the targeting signal. Mitochondria-targeting signals also include tri-phenyl-phosphonium (TPP) and guanidinium-based moieties. FIG. 13 shows the structures of mitochondria-targeting signals (A) tri-phenyl-phosphonium (TPP) and (B) guanidinium. Choline esters may also be used as a mitochondria-targeting signal. Tri-phenyl-phosphonium (TPP) derivative compounds, or TPP-derivatives, may also serve as mitochondria-targeting signals. The TPP-derivative compound may be, for example, one or more of the compounds shown in FIG. 12B, which include: 1. 2-butene-1,4-bis-TPP; 2. 2-chlorobenzyl-TPP; 3. 3-methylbenzyl-TPP; 4. 2,4-dichlorobenzyl-TPP; 5. 1-naphthylmethyl-TPP; or p-xylylenebis-TPP. The TPP-derivative compound comprises 2-butene-1,4-bis-TPP in some preferential embodiments. In some embodiments, there may be more than one TPP-derivative. In some embodiments, the TPP-derivative compound is one or more of: derivatives of 2-butene-1,4-bis-TPP; derivatives of 2-chlorobenzyl-TPP; derivatives of 3-methylbenzyl-TPP; derivatives of 2,4-dichlorobenzyl-TPP; derivatives of 1-naphthylmethyl-TPP; and derivatives of p-xylylenebis-TPP. Additional TPP-derivative structures are shown in FIGS. 11A-11C.

It should be appreciated that the foregoing list is not a comprehensive list of mitochondria-targeting signals, and that an unlisted mitochondria-targeting signal may be used without departing from the present approach. For example, an mDIVI-1 derivative may include one or more membrane-targeting signals and mitochondria-targeting signals as an R group. As a result, the mDIVI-1 derivative having one or more targeting signals will have enhanced uptake at the target organelle (e.g., CSC mitochondria), as opposed to unmodified mDIVI-1. TPP and TPP-derivatives are examples of lipophilic cations. Other lipophilic cations may be used as mitochondria-targeting signals. For example, one or more R groups may be 10-N-nonyl acridine orange, a lipophilic cation having the structure shown below:

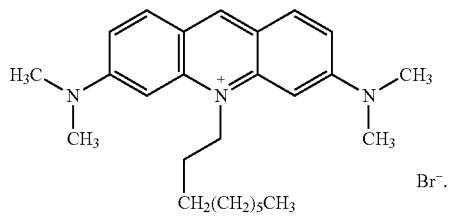

It should be appreciated that the present approach is not limited to the examples of lipophilic cations provided herein.

MDIVI-1 and its derivatives may be used to selectively eradicate CSCs, treat and/or prevent tumor recurrence, metastasis, drug resistance, and/or radiotherapy resistance. Mitochondrial division inhibitor-1 is a small molecule that selectively and reversibly inhibits DRP1. MDIVI-1 has been shown to target DRP1 by binding and suppressing both the DRP1 self-assembly into ring-like structures around the mitochondria and its capacity to catalyze GTP hydrolysis. MDIVI-1 prompts a rapid formation of interconnected mitochondria without overtly affecting other cellular structures such as the cytoskeleton or the endoplasmic reticulum. The IC50 of mDIVI-1 ranges from 1 to 50 µM, depending on the cell type. In contrast to the cytoprotective effect in neurons and cardiovascular cells, mDIVI-1 has a cytotoxic effect in hyperproliferative cancer cells and immortalized cell lines. Indeed, high DRP1 expression or activation has been described in several malignancies, and it promotes mitochondrial fission in cancer cells, which plays an important role in their proliferation and metastatic capacity. Reversal of that mitochondrial fission via DRP1 inhibition with mDIVI-1 induces apoptosis via cytochrome-c release and cell cycle arrest by impairing the assembly of mitotic spindles and cytokinesis, consequently leading to aneuploidy.

The following paragraphs assess the effects of mDIVI-1 and mDIVI-1 derivatives on mitochondrial function and CSC behavior.

MDIVI-1 Treatment Reduces MCF7 Cell Viability

Figure 2:
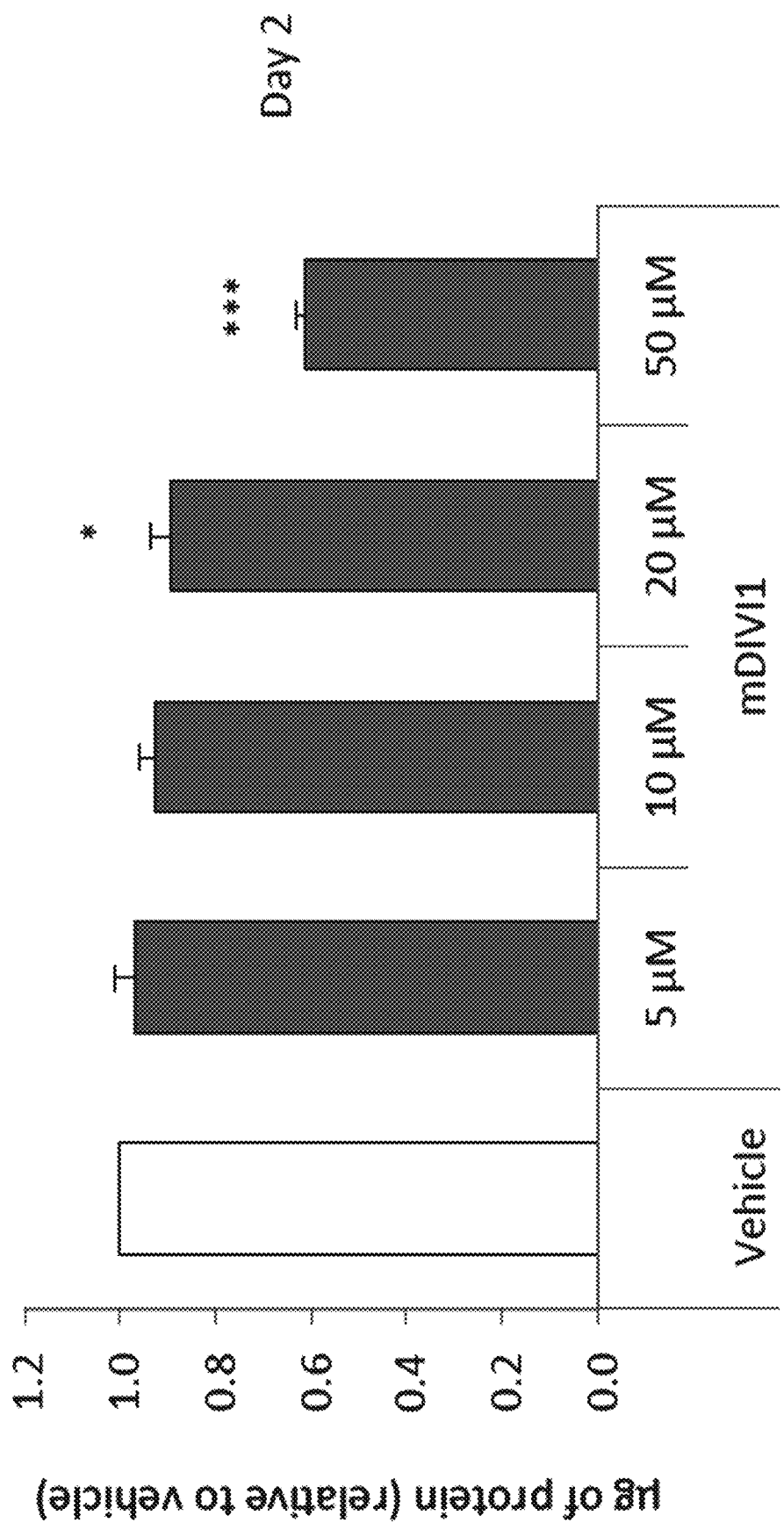
FIG. 2 shows results of the Bradford assay on protein content of MCF7 cells treated with mDIVI-1.

The inventors sought to evaluate whether mDIVI-1-induced inhibition of DRP1 has repercussion on the viability of MCF7 cells. FIG. 1 shows the results of a reazurin-based viability assay Presto-Blue, where lighter bars represent 2-day exposure, and darker bars represent 5-day exposure. The data demonstrates that exposure to mDIVI-1 for 48 hours did not decrease viability of MCF7 cells at a concentration of 10 µM, and significantly reduced it by 20% at 50 µM and 100 µM. Similar results were obtained using the Bradford assay, which measures protein content, as an indicator of cell viability. FIG. 2 shows results of the Bradford assay. Only exposure to higher concentrations of mDIVI-1 (20 and 50 µM) significantly reduced MCF7 protein content after 2 days of treatment. The data also shows that five days of treatment resulted in a larger impact on MCF7 cell viability, significantly diminishing it by 20% at a concentration of 10 µM, by over 65% at 50 µM and 85% at 100 µM. Thus, mDIVI-1 reduces the viability of MCF7 cells mostly at higher concentrations and after 5 days of treatment in the preliminary assays.

MDIVI-1 Increases MCF7 Mitochondrial Mass and Mitochondrial Oxidative Stress

Figure 3:
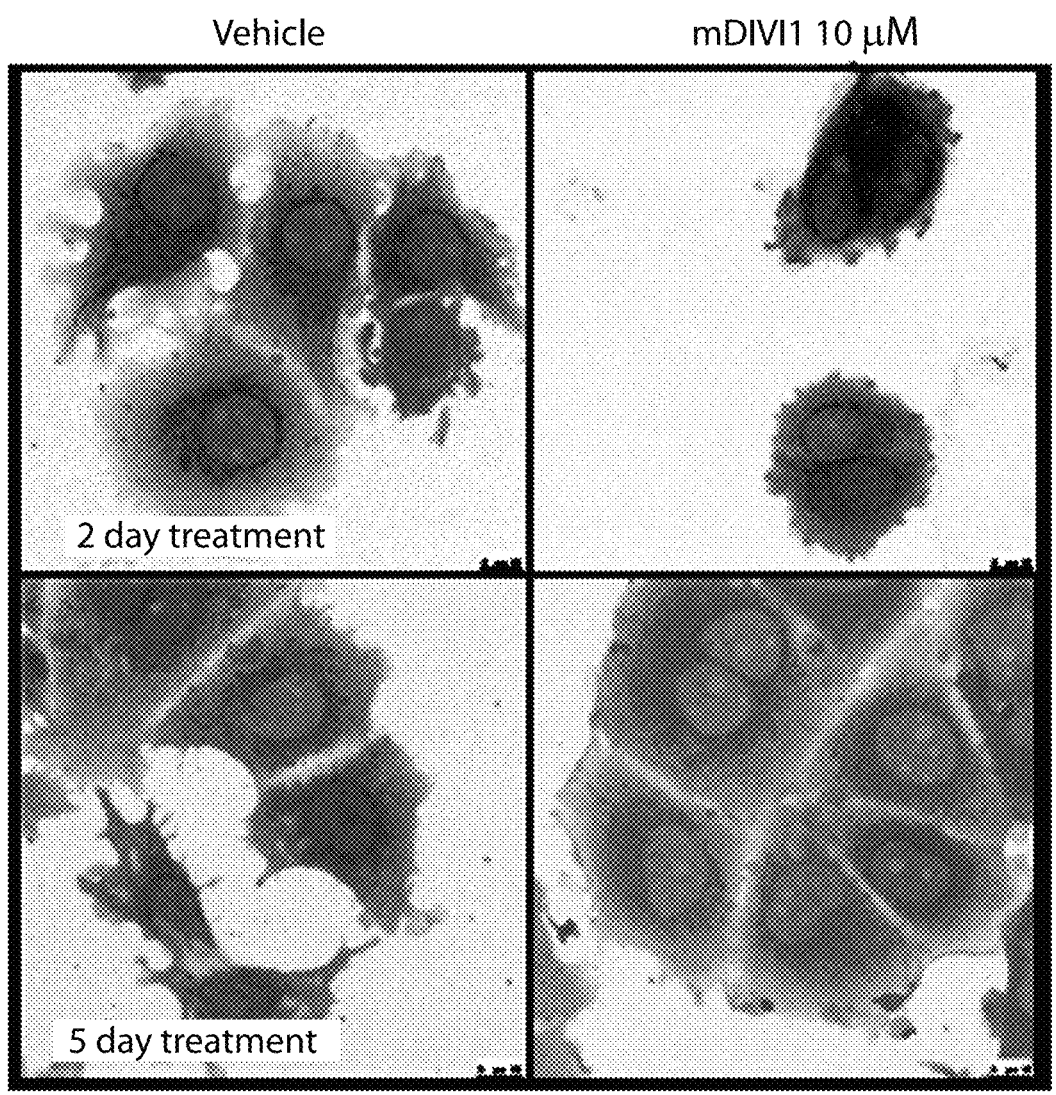
FIG. 3 is a collection of images taken after Mitotracker Deep Red staining (inverted colors for reproducibility), comparing a control with mDIVI-1 at 10 µM over 2- and 5-day treatment.
Figure 4A:
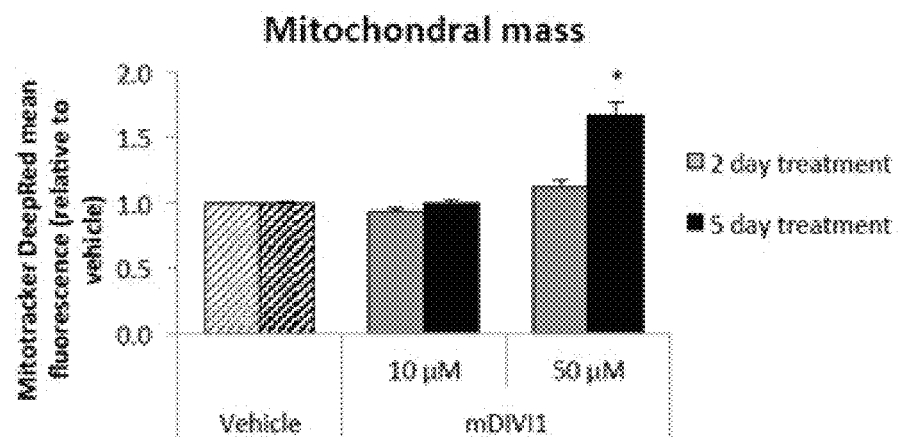
FIGS. 4A-4C show mitochondrial mass, mitochondrial superoxide, and reactive oxygen species data for control and mDIVI-1 treatment, over 1-day, 2-day, and 5-day exposure.
Figure 4B:
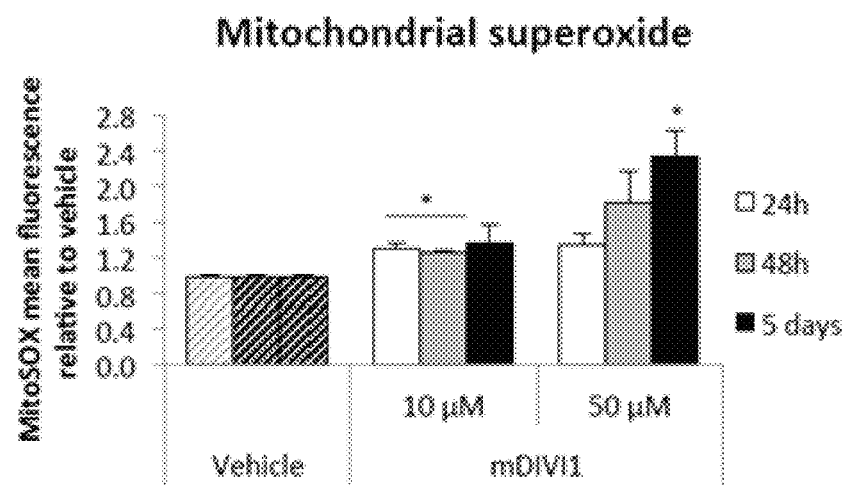
Figure 4C:
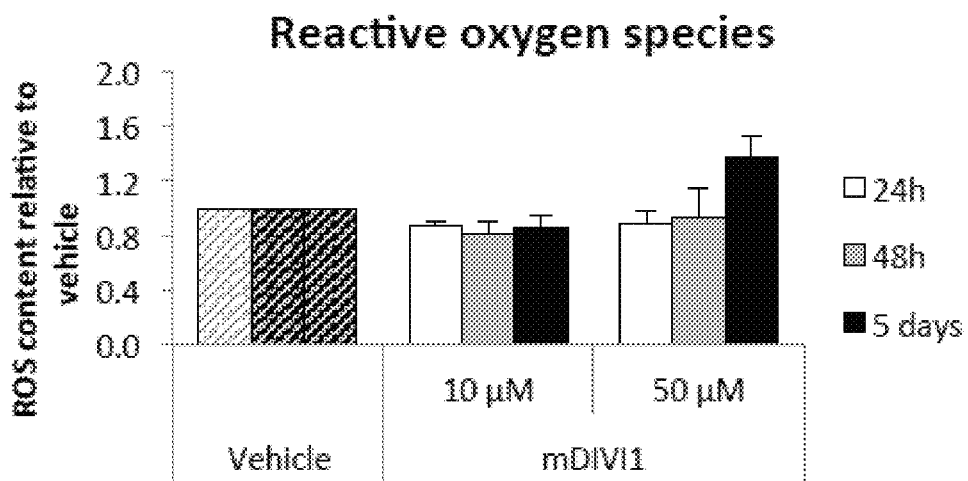

In order to assess whether the inhibition of DRP1 was actually being translated into a reduction in mitochondrial fission, the inventors stained the mitochondria of MCF7 cells with Mitotracker Deep Red, which is a marker of mitochondrial mass. MDIVI-1 treatment led to more interconnected mitochondria, with slightly increased mitochondrial calibres, which could be a result of the absence of fission activity. FIG. 3 is a collection of images taken after the staining, and compares the control with mDIVI-1 at 10 µM over 2- and 5-day treatment. The original images are black background with shades of red over the cells, whereas the images in FIG. 3 have been color-inverted and generated in grey scale. Mitochondrial mass was also quantified by flow cytometry. FIGS. 4A-4C show results of mitochondrial mass quantification. In FIG. 4A, Mitotracker Deep Red mean intensity relative to vehicle intensity is shown for 2-day and 5-day treatments. FIG. 4B shows the mean fluorescence intensity of mitochondrial superoxide relative to vehicle intensity, over 1-day, 2-day, and 5-day exposure. FIG. 4C shows reactive oxygen species content relative to the vehicle over the same exposure durations. Mitotracker Deep Red mean fluorescence intensity was found to be significantly higher after 5 days of treatment with 50 μM mDIVI-1, indicating that at higher concentrations, mDIVI-1 inhibited DRP1 and resulted in an increase in the mitochondrial mass of MCF7 cells.

Inhibition of the mitochondrial fission impacts on other mitochondrial processes, such as mitochondrial metabolism and general and mitochondrial oxidative stress. To confirm, MCF7 cells were stained with MitoSOX and CM-H2DCFDA, and mitochondrial superoxide and total ROS were quantified by flow cytometry. As can be seen in FIG. 4B, MitoSOX staining quantification in MCF7 cells revealed that exposure to both concentrations of mDIVI-1 significantly increased mitochondrial superoxide production compared to vehicle-treated cells. However, general oxidative stress levels did not change after exposure to mDIVI-1. Only 5 days of treatment showed a slight trend toward an increase in the production of total ROS, as seen in FIG. 4C. Whereas the increase in general ROS goes in line with the increase in mitochondrial content, the boost in the levels of mitochondrial superoxide in mDIV1-treated cells is actually bigger than the observed increased mitochondrial content. The data confirm that mDIVI-1 treatment slightly increases mitochondrial mass and clearly induced the generation of mitochondrial superoxide without any major effects on MCF7 general oxidative stress.

Figure 5A:
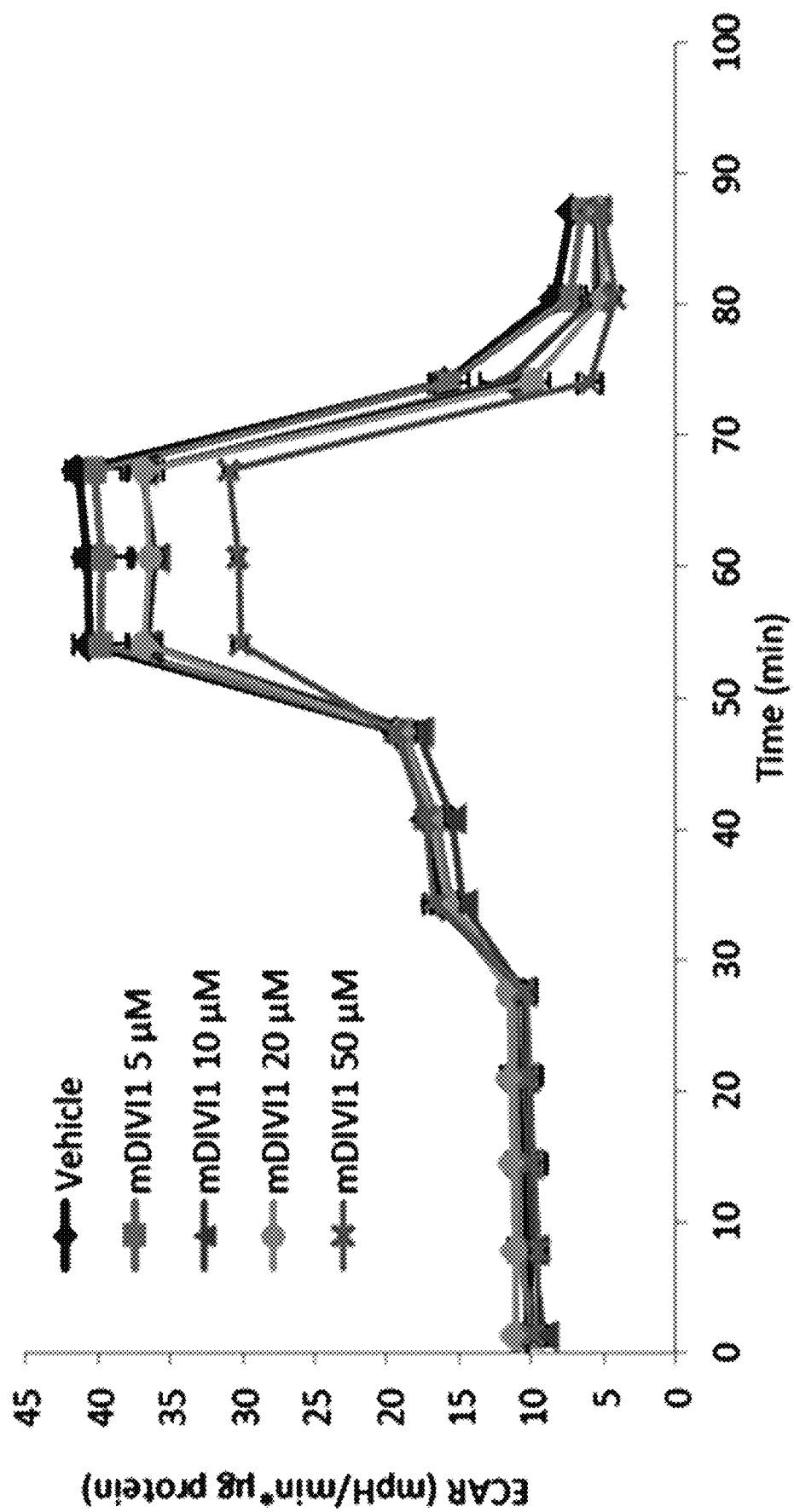
FIG. 5A shows ECAR of MCF7 cells for control and mDIVI-1 treatment.
Figure 5B:
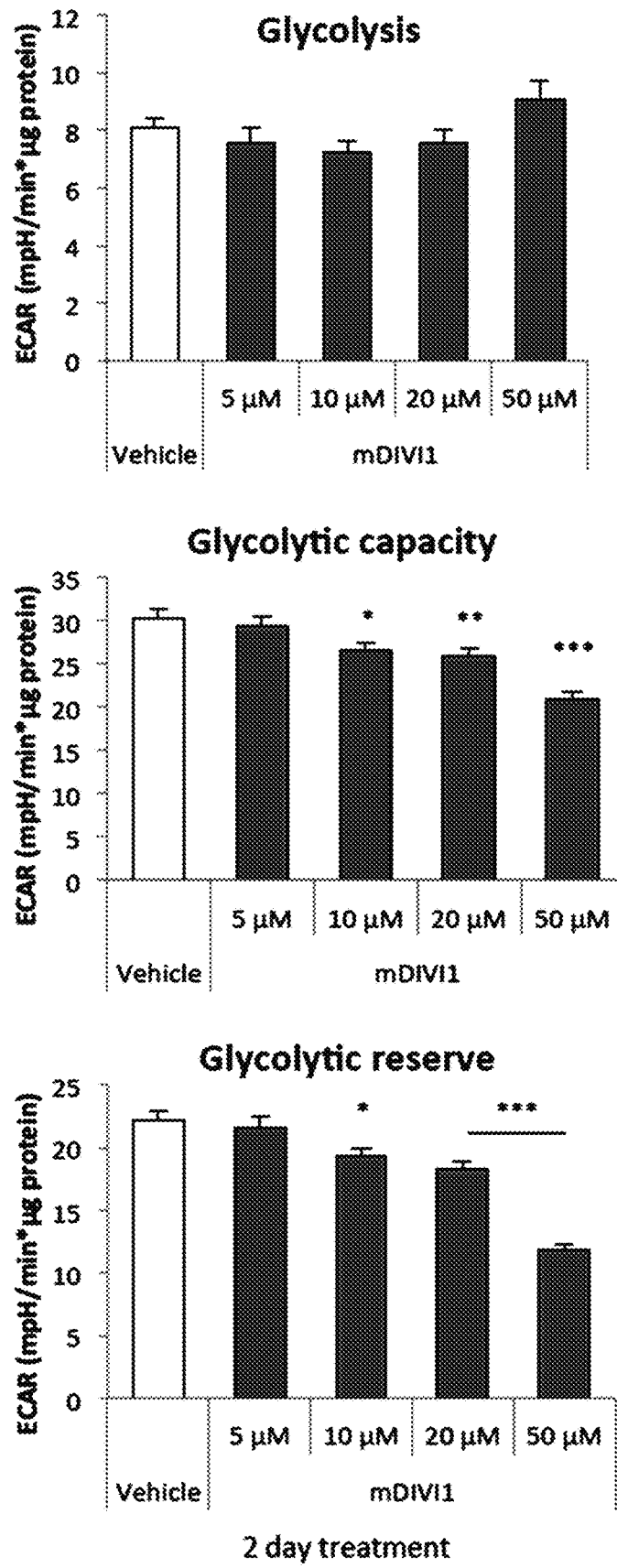
FIG. 5B are data for glycolysis, glycolytic capacity, and glycolytic reserve, for control and mDIVI-1 treatment.
Figure 6A:
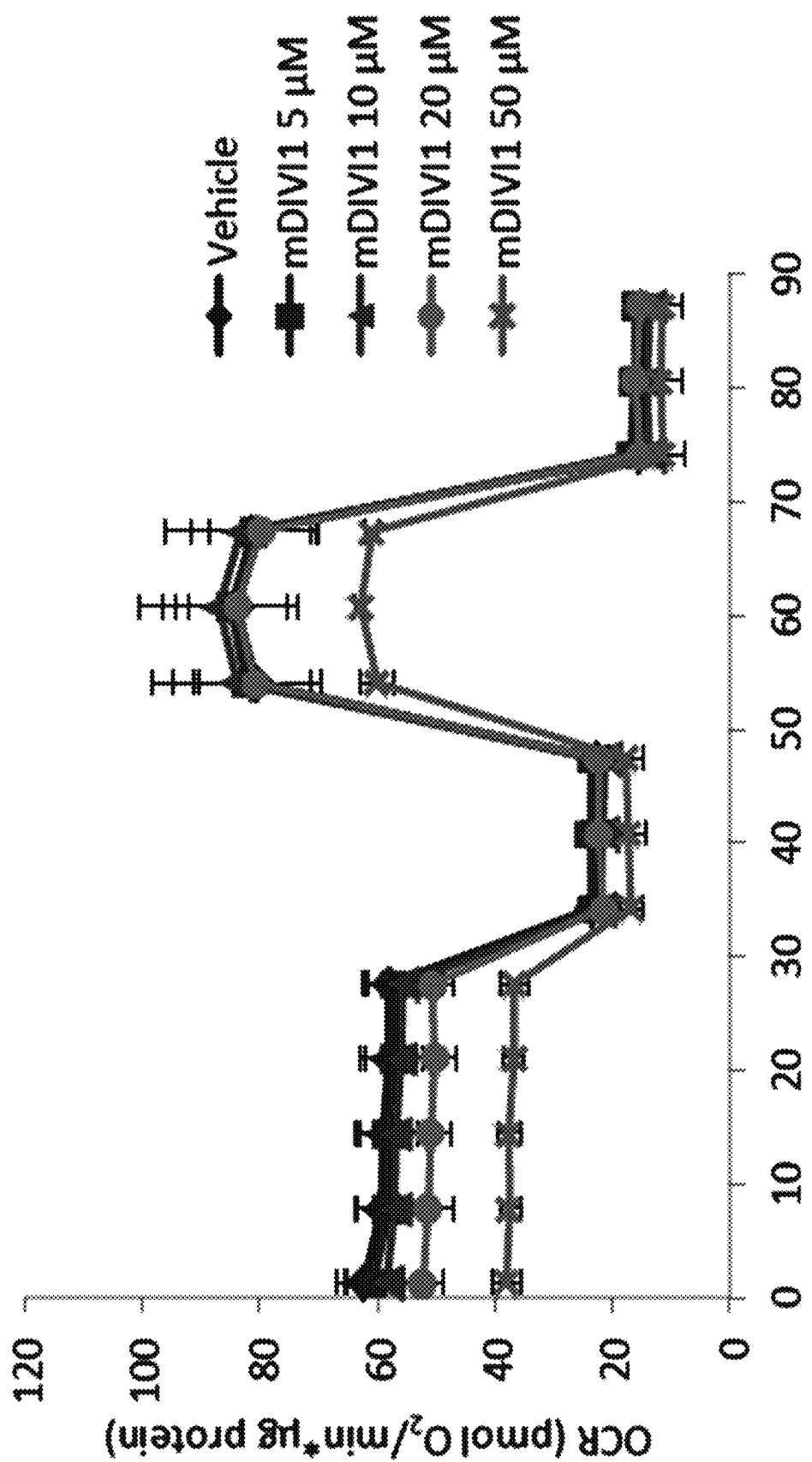
FIG. 6A shows OCR of MCF7 cells under control and for mDIVI-1 treatment.
Figure 6B:
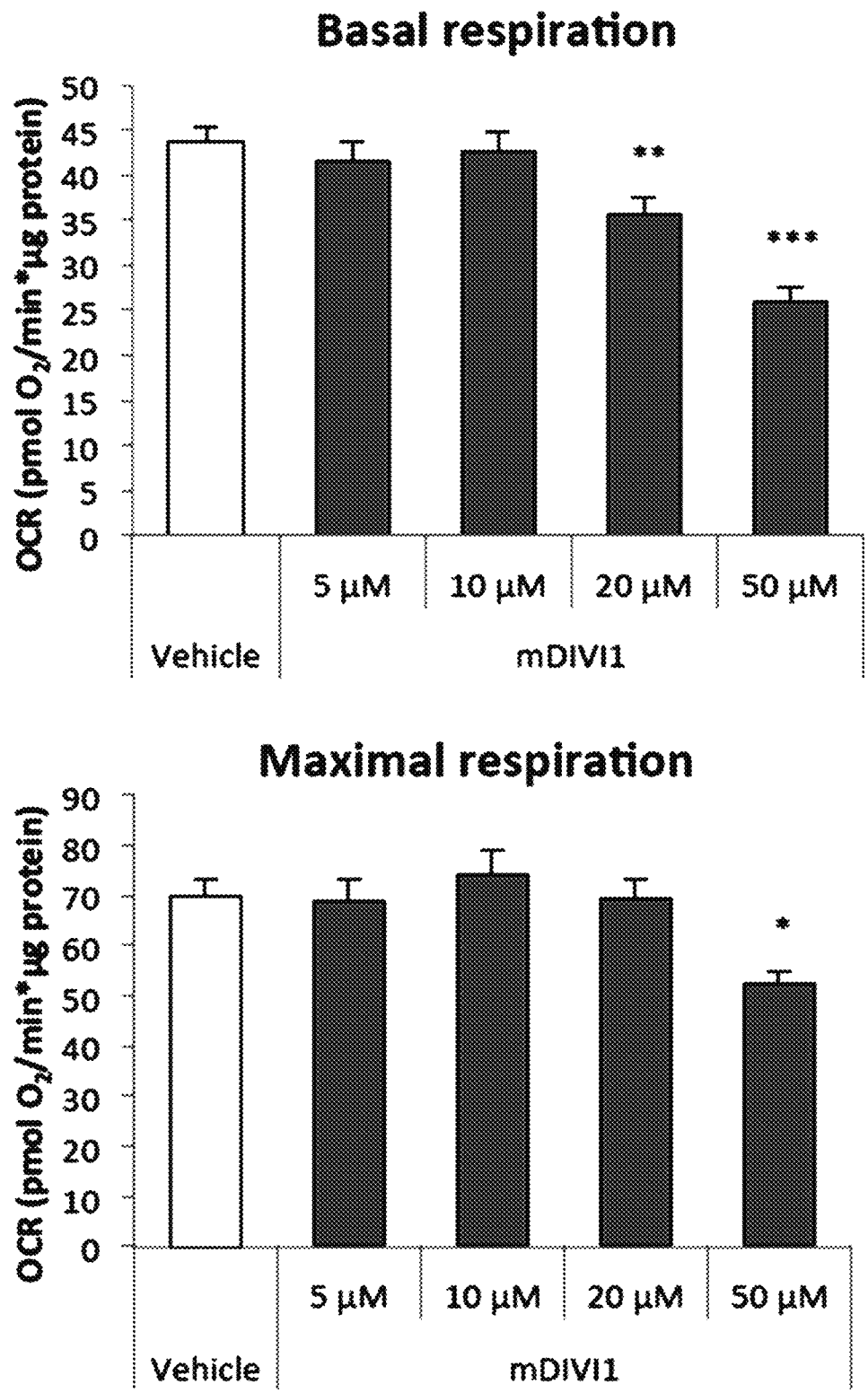
FIGS. 6B and 6C show respiration and ATP production data.
Figure 6C:
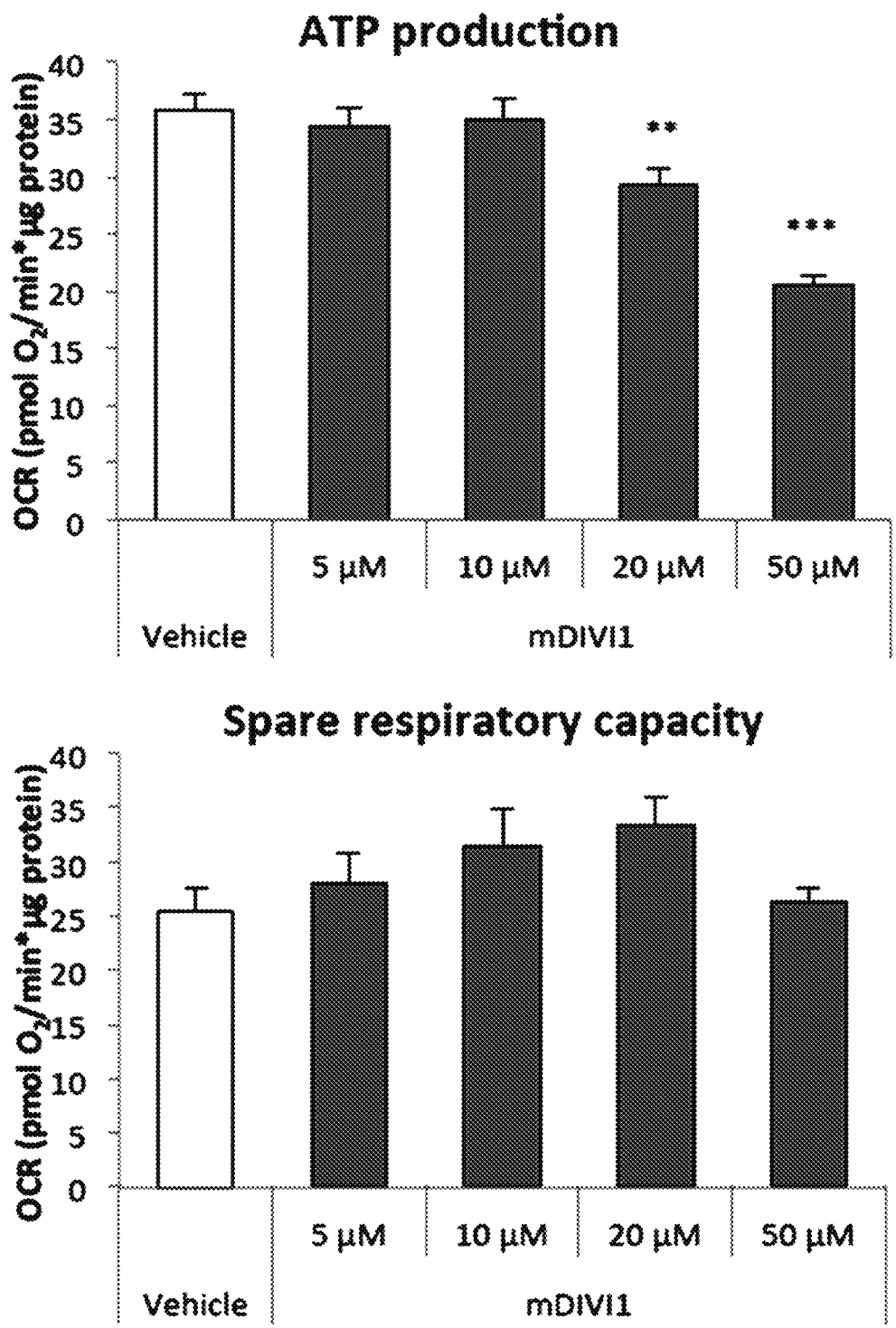
Figure 6D:
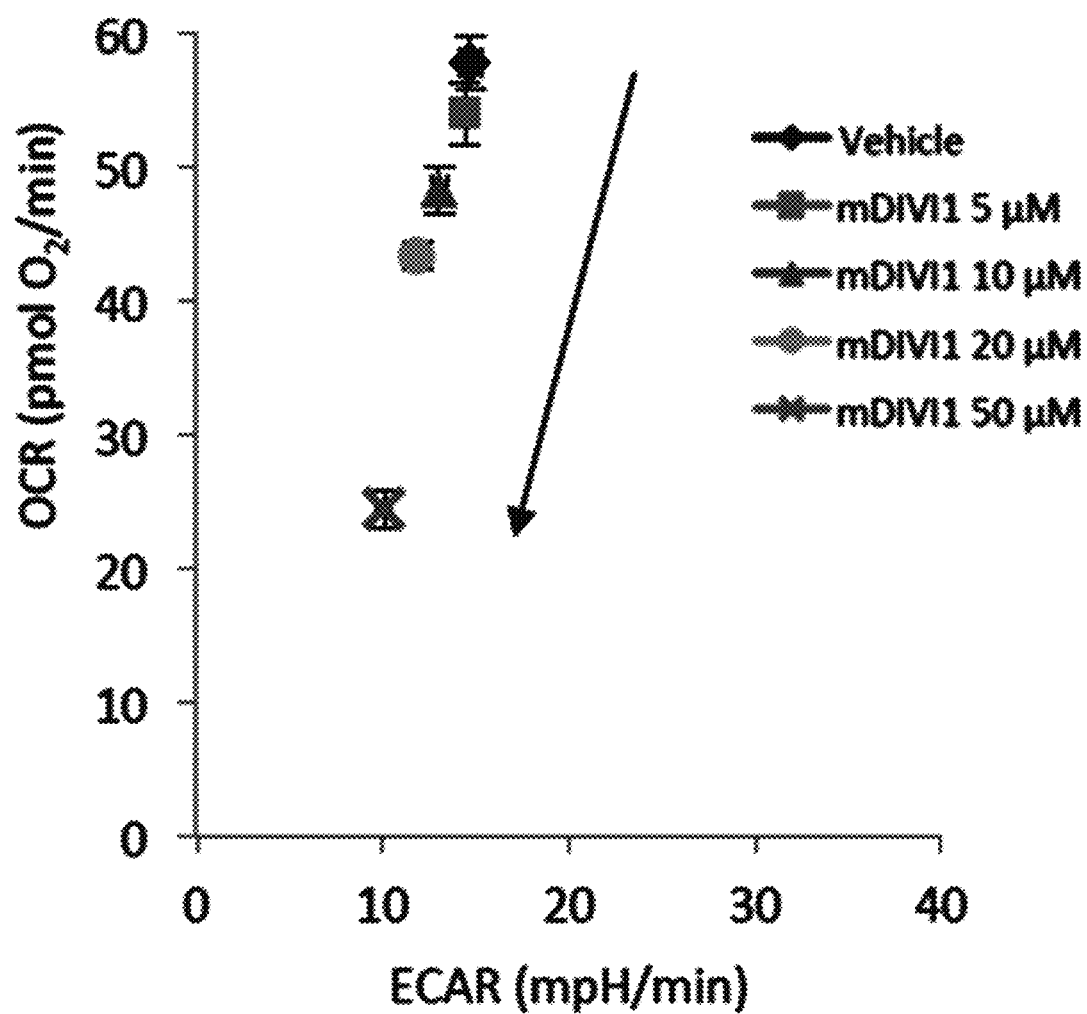
FIG. 6D shows the dose-dependent impact of mDIVI-1 treatment on OCR and ECAR.

MDIVI-1 Reduces Glycolytic Capacity, Respiration and ATP Production of MCF7 Cells Inhibition of mitochondrial fission by m-DIVI-1 or a derivative thereof also blocks the normal functioning of mitochondrial metabolism in CSCs. Indeed, it has been shown that a DRP1 mutant that inhibits mitochondrial fission increases glucose uptake and lactate production, and decreases ATP production. Thus, the inventors measured the glycolytical function and the mitochondrial respiration in MCF7 cells exposed to mDIVI-1. The extracellular acidification rate (ECAR) and the oxygen consumption rate (OCR) were measured using an XF96 Extracellular Flux Analyser, and FIGS. 5A, 5B, and 6A-6C show the data. Basal glycolysis, glycolytic capacity and glycolytic reserve were calculated after addition of glucose, oligomycin and 2-deoxyglucose (2DG) into the media. Surprisingly, exposure to MDIVI-1 did not have a significant effect on basal glycolysis. However, as seen in FIG. 5B, the glycolytic capacity and glycolytic reserve of MCF7 cells was reduced after treatment with mDIVI-1. That is, treatment with mDIVI-1 for 48 hours blocked the increase of the ECAR usually linked to the oligomycin-induced inhibition of mitochondrial complex V of the electron transport chain, indicating that mDIVI-1-treated MCF7 either have less ATP demand or have a less efficient mitochondrial oxidative phosphorylation than vehicle-treated cells. Thus, to measure basal respiration, ATP production, maximal respiration and spare respiratory capacity, oxygen consumption was also calculated after addition of oligomycin, FCCP and antimycin/rotenone into glucose-containing media. FIGS. 6B and 6C show that exposure to mDIVI-1 for 48 hours significantly reduced the oxygen consumption linked to basal respiration, ATP production and to a lesser extent, maximal respiration at higher concentrations. However, it slightly increased the spare respiratory capacity of MCF7 cells after treatment with all mDIVI-1 concentrations, suggesting that basal respiration in mDIVI-1-treated is further from its theoretical maximum than vehicle-treated cells. The OCR versus ECAR graph was also plotted to have an indication of the metabolic state of the cell. FIG. 6D shows that mDIVI-1 treatment also decreased dose-dependently the OCR/ECAR ratio of MCF7 cells compared to vehicle, indicating that mDIVI-1-treated MCF7 cells are less aerobic and metabolically less active. Thus, mDIVI-1-induced inhibition of mitochondrial fission functionally targets oxidative phosphorylation and also the glycolytic function of MCF7 cells, transforming them into cells with lower mitochondrial energetic needs.

TABLE 1

Changes in the expression of enzymes involved in several cellular metabolic pathways after exposure of MCF7 cells to mDIVI-1 for 48 hours as measured by label-free quantitative proteomics.

| | | 10 μM mDIVI-1 |
|---|---|---|
| Glycolysis | | |
| Hexokinase 1 | HK1 | ↓ Infinite |
| Fructose-bisphosphate aldolase A | ALDOA | ↓ 2.88 |
| Enolase 1 | ENO1 | ↓ 6.63 |
| Post-Glycolysis Processes | | |
| Pyruvate dehydrogenase | PDHB | ↑ 1.63 |
| Pentose Phosphate Pathway | | |
| 6-phosphogluconolactonase | PGLS | ↓ 1.56 |
| Phosphogluconate dehydrogenase | PGD | ↓ 3.91 |
| Transketolase | TKT | ↑ 2.06 |
| TCA Cycle | | |
| Citrate synthase, mitochondrial | CS | ↓ 1.51 |
| Isocitrate dehydrogenase | IDH2 | ↑ 1.84 |
| | IDH3G | ↓ 1.51 |

TABLE 1-continued

Changes in the expression of enzymes involved in several cellular metabolic pathways after exposure of MCF7 cells to mDIVI-1 for 48 hours as measured by label-free quantitative proteomics.

| | | 10 μM mDIVI-1 |
|---|---|---|
| Oxidative Phosphorylation | | |
| NADH dehydrogenase (complex I) | NDUFV1 | ↓ 1.63 |
| | MT-ND5 | ↑ 1.84 |
| Coenzyme Q - cytochrome c reductase (complex III) | UQCRC1 | ↓ 2569.35 |
| Cytochrome c oxidase (complex IV) | COX6A1 | ↑ 1.70 |
| ATP synthase (complex V) | ATP5O | ↓ 13.56 |
| Fatty Acid Oxidation | | |
| Acetyl-Coenzyme A acyltransferase 1, peroxisomal | ACAA1 | ↑ 3.96 |
| Acetyl-Coenzyme A acyltransferase 2, mitochondrial | ACAA2 | ↓ 2.09 |
| Long-chain-aldehyde dehydrogenase | ALDH3A2 | ↑ 4.40 |
| Delta-1-pyrroline-5-carboxylate dehydrogenase, mitochondrial | ALDH4A1 | ↑ 2.40 |
| 4-trimethylaminobutyraldehyde dehydrogenase | ALDH9A1 | ↑ 1.72 |
| Acyl-CoA dehydrogenase family member 9, mitochondrial | ACAD9 | ↓ 1.94 |
| Carnitine O-palmitoyltransferase 2, mitochondrial | CPT2 | ↑ 3.15 |
| Fatty Acid Synthesis | | |
| Fatty acid synthase | FASN | ↑ 1.97 |
| Beta-ketoacyl-ACP synthase | OXSM | ↓ 1.61 |
| Ketolysis/Ketogenesis | | |
| Acetyl-CoA acetyltransferase, mitochondrial | ACAT1 | ↓ 2.40 |
| 3-oxoacid CoA-transferase 1, mitochondrial | OXCT1 | ↑ 1.64 |
| 3-hydroxy-3-methylglutaryl-CoA synthase 1 | HMGCS1 | ↑ 4.09 |
| Lipid Metabolism (Other) | | |
| short/branched chain specific acyl-CoA dehydrogenase | ACADSB | ↓ 2.92 |
| Cytochrome P450 1B1 | CYP1B1 | ↑ 19.96 |
| Cytochrome P450, family 1, subfamily A, polypeptide 1 | CYP1A1 | ↑ 190.30 |
| Lanosterol 14 α-demethylase | CYP51A1 | ↑ 3.41 |
| Lanosterol synthase | LSS | ↓ 1.82 |
| Farnesyl-diphosphate farnesyltransferase 1 | FDFT1 | ↓ 1.50 |
| Isopentenyl-diphosphate delta isomerase | IDI1 | ↓ 1.79 |

To identify differentially regulated proteins upon treatment with mDIVI-1, MCF7 cells were exposed for 48 hours to either vehicle or 10 μM mDIVI-1 and cell lysates were subject to label-free quantitative proteomics. Following protein digestion with trypsin, peptide fractions were processed on an LTQ-Orbitrap XL mass spectrometer. Those peptides identified were further analyzed to find proteomic changes between mDIVI-1-treated and vehicle-treated MCF7 cells, as described before. To define differential regulation, those identified proteins that showed a fold change difference of 1.5 or higher, and p values of <0.05 (ANOVA) compared to vehicle were considered. First, the inventors searched the proteomics datasets for changes in proteins involved in metabolism. The results are set forth in Table 1, above. The expression of several glycolytic enzymes, as well as pentose phosphate pathway enzymes and enzymes involved in mitochondrial metabolism were found to be down-regulated in mDIVI-1-treated MCF7 cells compared to vehicle treatment. Of note, hexokinase, which generates glucose 6-phosphate from glucose for the glycolytic and the pentose phosphate pathways, was infinitely down-regulated. In fact, the first two enzymes of the oxidative branch of the pentose phosphate pathway were also found downregulated in cells treated with m-DIVI-1, compared to vehicle-treated cells (as seen in Table 1). That may possibly translate into a loss of antioxidant power, as the pentose phosphate pathway is a major source of NADPH. Furthermore, components of the complex III and V of the electron transport chain were found to be highly downregulated in mDIVI-1-treated MCF7 cells (Table 1).

TABLE 2

Pathway analysis of differentially expressed proteins in MCF7 cells treated with mDIVI-1 compared to vehicle-treated cells

| Ingenuity Canonical Pathways | -log(p-value) | Z score | Ratio |
|---|---|---|---|
| Remodeling of Epithelial Adherens Junctions | 13.6 | −0.30 | 0.348 |
| Actin Cytoskeleton Signaling | 11.5 | −1.15 | 0.176 |
| Germ Cell-Sertoli Cell Junction Signaling | 9.79 | | 0.183 |
| EIF2 Signaling | 9.4 | −0.83 | 0.173 |
| Epithelial Adherens Junction Signaling | 8.9 | | 0.189 |
| Tight Junction Signaling | 8.68 | | 0.175 |
| Integrin Signaling | 8.46 | −0.36 | 0.156 |
| ILK Signaling | 8.38 | 0.73 | 0.161 |

TABLE 2-continued

Pathway analysis of differentially expressed proteins in MCF7 cells treated with mDIVI-1 compared to vehicle-treated cells

| Ingenuity Canonical Pathways | -log(p-value) | Z score | Ratio |
|---|---|---|---|
| Regulation of eIF4 and p70S6K Signaling | 8.17 | −1.41 | 0.175 |
| Paxillin Signaling | 7.85 | −0.69 | 0.2 |
| Caveolar-mediated Endocytosis Signaling | 7.42 | | 0.239 |
| Sertoli Cell-Sertoli Cell Junction Signaling | 7.07 | | 0.156 |
| Regulation of Actin-based Motility by Rho | 6.77 | −0.73 | 0.207 |
| Phagosome maturation | 6.61 | | 0.178 |
| Clathrin-mediated Endocytosis Signaling | 6.48 | | 0.143 |
| Regulation of Cellular Mechanics by Calpain Protease | 5.75 | −2.24 | 0.236 |
| RhoA Signaling | 5.26 | −0.94 | 0.158 |
| Mitotic Roles of Polo-Like Kinase | 5.05 | 0.82 | 0.206 |
| RhoGDI Signaling | 4.95 | 0.85 | 0.134 |
| Protein Ubiquitination Pathway | 4.71 | | 0.114 |
| Role of BRCA1 in DNA Damage Response | 4.66 | | 0.179 |
| Leukocyte Extravasation Signaling | 4.62 | −0.63 | 0.122 |
| mTOR Signaling | 4.53 | 0.63 | 0.123 |
| Actin Nucleation by ARP-WASP Complex | 4.15 | −1.51 | 0.196 |
| FAK Signaling | 4.1 | | 0.153 |
| DNA Double-Strand Break Repair by Non-Homologous End Joining | 3.42 | | 0.357 |
| Signaling by Rho Family GTPases | 3.35 | −0.41 | 0.102 |
| Estrogen Receptor Signaling | 3.29 | | 0.125 |
| Superpathway of Cholesterol Biosynthesis | 2.79 | | 0.222 |
| Cleavage and Polyadenylation of Pre-mRNA | 2.69 | | 0.333 |
| AMPK Signaling | 2.66 | −0.63 | 0.101 |
| Palmitate Biosynthesis I | 2.62 | | 1 |
| Fatty Acid Biosynthesis Initiation II | 2.62 | | 1 |
| Calcium Signaling | 2.39 | −0.81 | 0.1 |
| Cdc42 Signaling | 2.37 | −0.83 | 0.109 |
| Rac Signaling | 2.36 | −0.83 | 0.112 |
| Telomere Extension by Telomerase | 2.3 | | 0.267 |
| RAN Signaling | 2.19 | | 0.25 |
| Assembly of RNA Polymerase I Complex | 2.11 | | 0.333 |
| ERK/MAPK Signaling | 2.07 | −0.47 | 0.0909 |
| Cell Cycle Control of Chromosomal Replication | 2.04 | | 0.185 |
| PAK Signaling | 2.02 | −0.30 | 0.11 |
| Protein Kinase A Signaling | 2.01 | −1.61 | 0.0775 |
| Apoptosis Signaling | 1.97 | −1.26 | 0.114 |
| Pentose Phosphate Pathway | 1.97 | | 0.3 |
| Death Receptor Signaling | 1.88 | −1.26 | 0.11 |
| Unfolded protein response | 1.85 | | 0.132 |
| DNA Methylation and Transcriptional Repression Signaling | 1.83 | | 0.2 |
| Mevalonate Pathway I | 1.74 | | 0.25 |
| Ephrin Receptor Signaling | 1.67 | −1.39 | 0.0872 |
| Agranulocyte Adhesion and Diapedesis | 1.61 | | 0.0857 |
| GM-CSF Signaling | 1.59 | −0.38 | 0.11 |
| Axonal Guidance Signaling | 1.56 | | 0.0703 |
| Gap Junction Signaling | 1.52 | | 0.0854 |
| Ketolysis | 1.37 | | 0.286 |
| CDK5 Signaling | 1.3 | −1.34 | 0.0918 |

To obtain additional functional insights into pathways that are differentially regulated in MCF7 cells treated with mDIVI-1, bioinformatics analysis of the proteomics datasets were conducted. All proteins were analyzed using the Ingenuity Pathway Analysis software (IPA) to seek altered canonical pathways and toxicity functions. Of note, amongst the altered pathways identified by IPA in the cells treated with mDIVI-1 were pathways involved in metabolism such as pentose phosphate pathway, mTOR signaling, AMPK and protein kinase A signaling, fatty acid biosynthesis, cholesterol and palmitate biosynthesis, mevalonate pathway and ketolysis. Likewise, the toxicity functions found to be altered in MCF7 cells treated with mDIVI-1 compared with vehicle treatment included decreases in permeability transition of mitochondria and mitochondrial membrane, fatty acid metabolism and cholesterol biosynthesis, as set forth in Table 2. Thus, besides mitochondrial respiration and glycolysis, fatty acid metabolism also seems to be altered in MCF7 cells treated with mDIVI-1, as observed by label-free quantitative proteomics.

MDIVI-1 Reduces Tumorsphere Formation in MCF7 Breast Cancer, A375 Melanoma and A549 Lung Cancer Cell Lines CSCs depend on mitochondrial metabolism for their survival and propagation. As mDIVI-1 functioned as an inhibitor of mitochondrial oxidative phosphorylation in MCF7 breast cancer cells, the inventors confirmed the effects of this mitochondrial fission inhibitor on the behavior of CSCs.

Figure 7A:
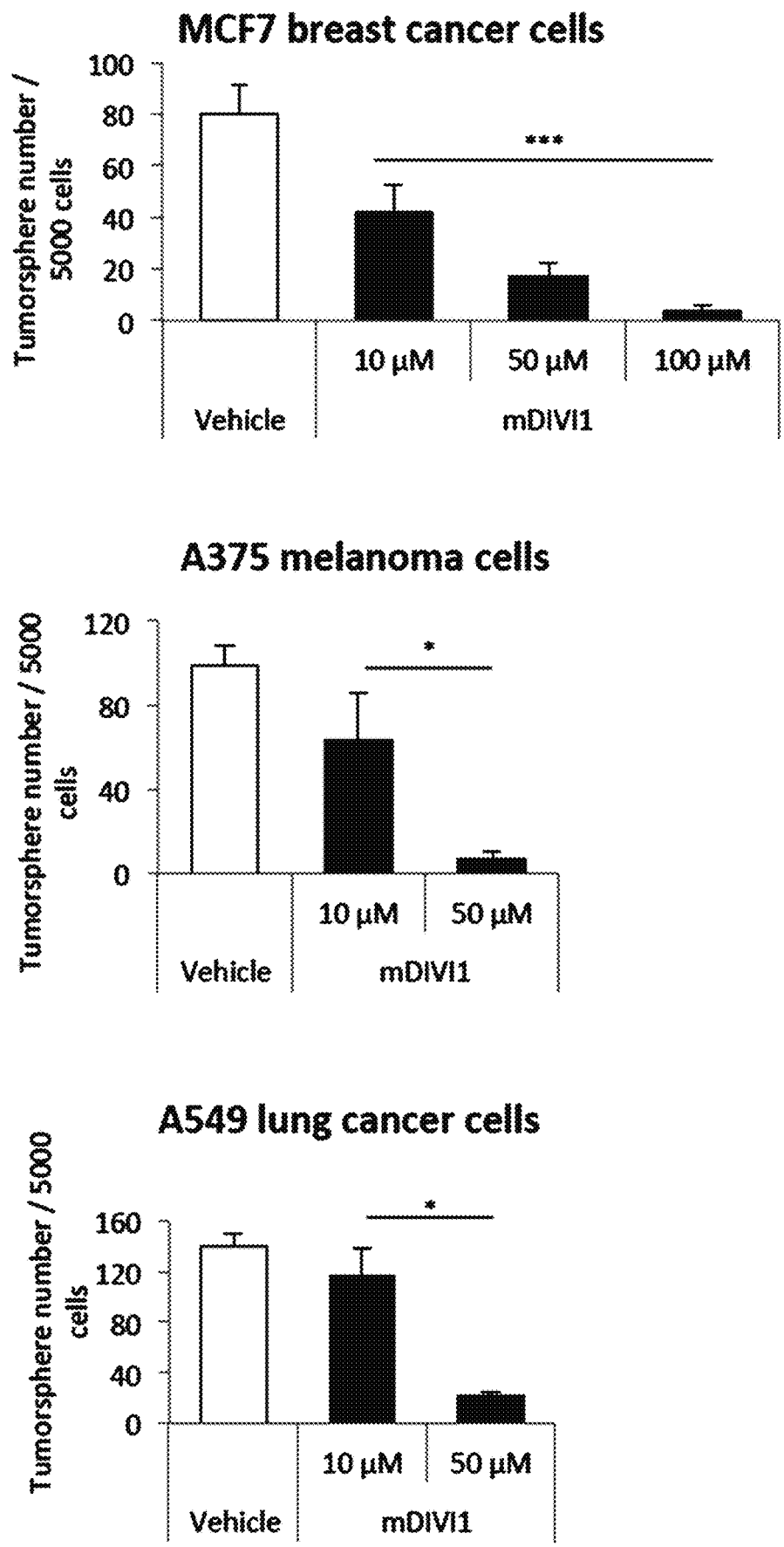
FIG. 7A shows the impact of mDIVI-1 treatment on tumorsphere formation in various cancer cells.
Figure 7B:
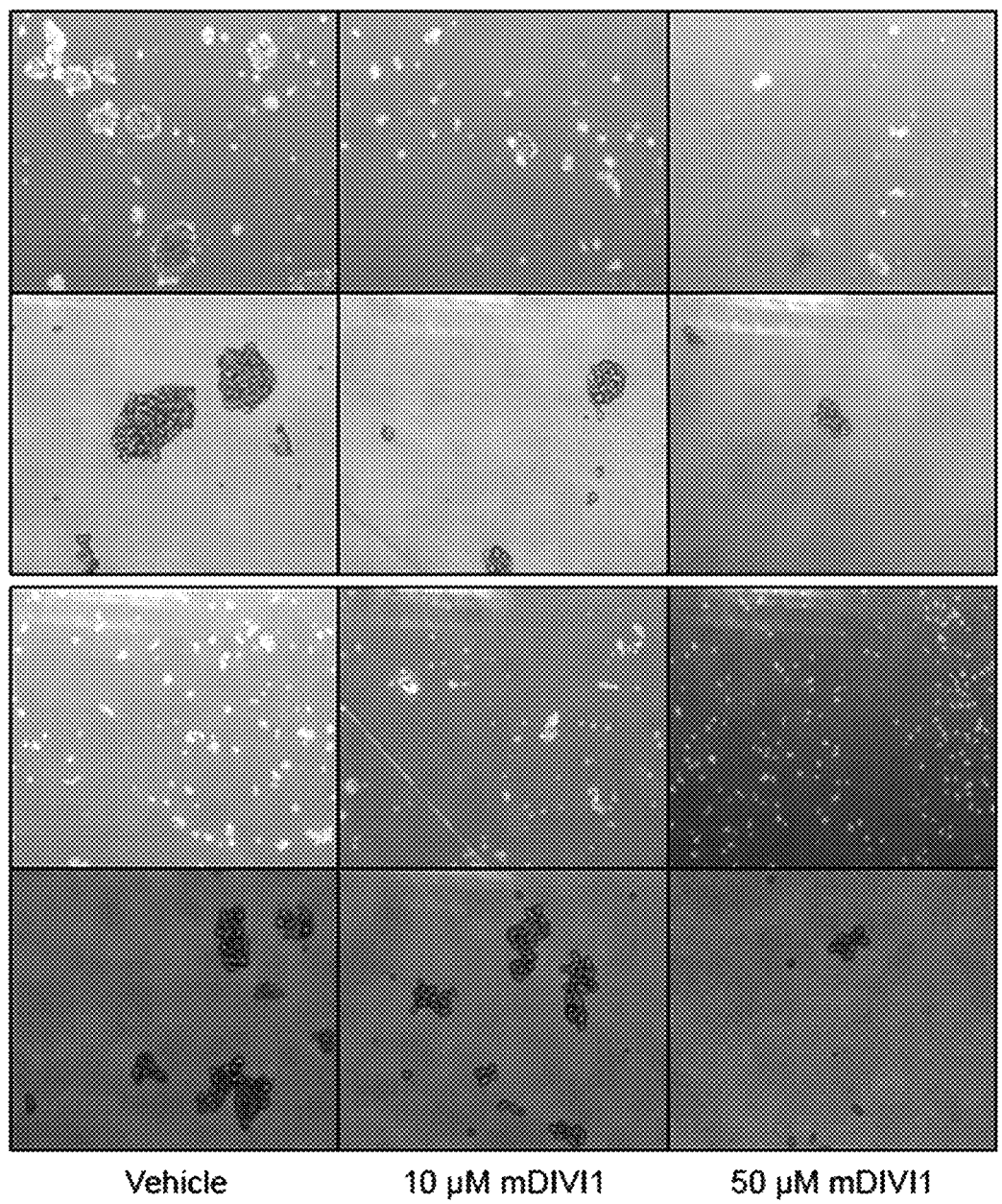
FIG. 7B shows images of A375 melanoma and A549 lung tumorspheres after treatment.
Figure 8A:
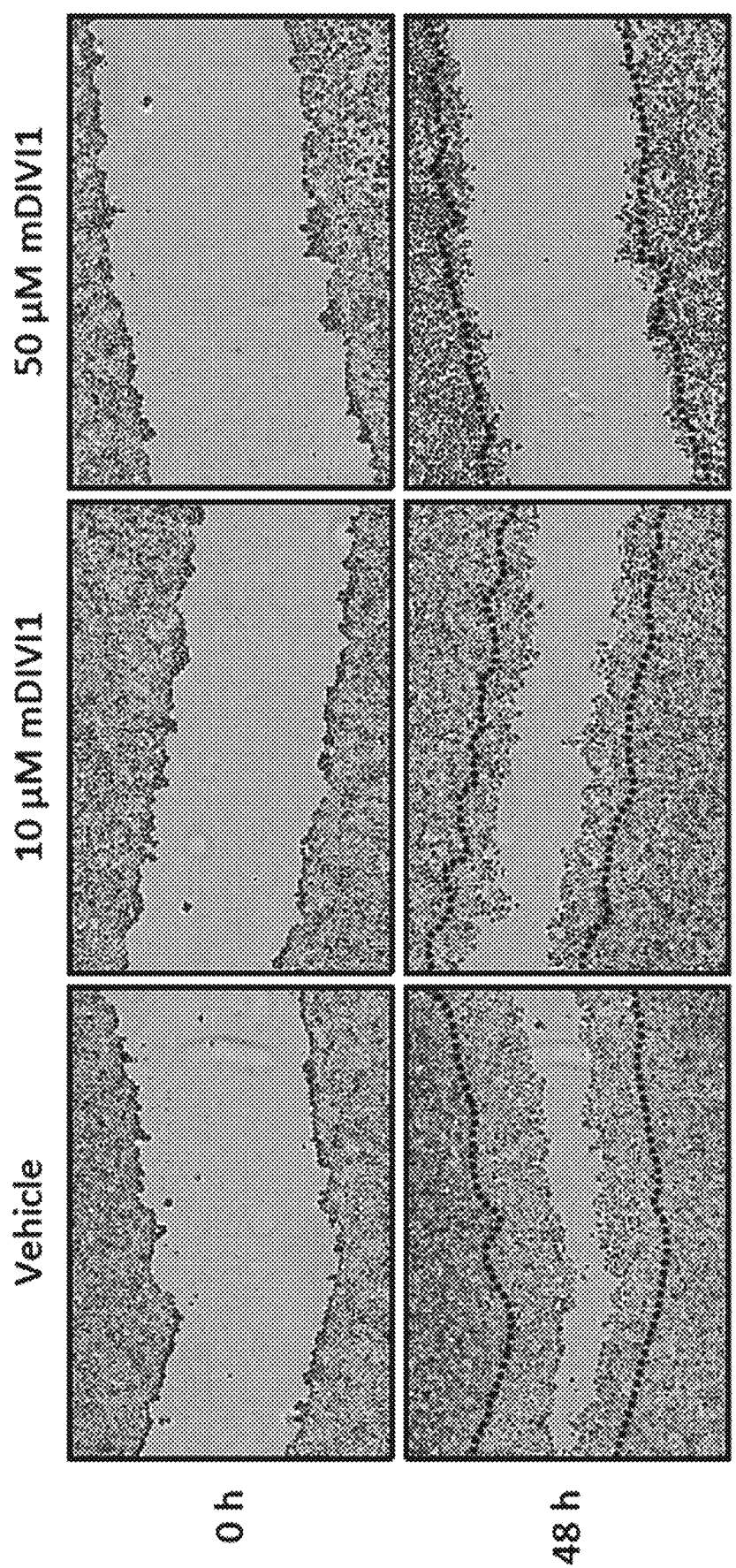
FIG. 8A shows images of MCF7 scratch assays with mDIVI-1 treatment, and FIG. 8B summarizes wound closure percentage.
Figure 8B:
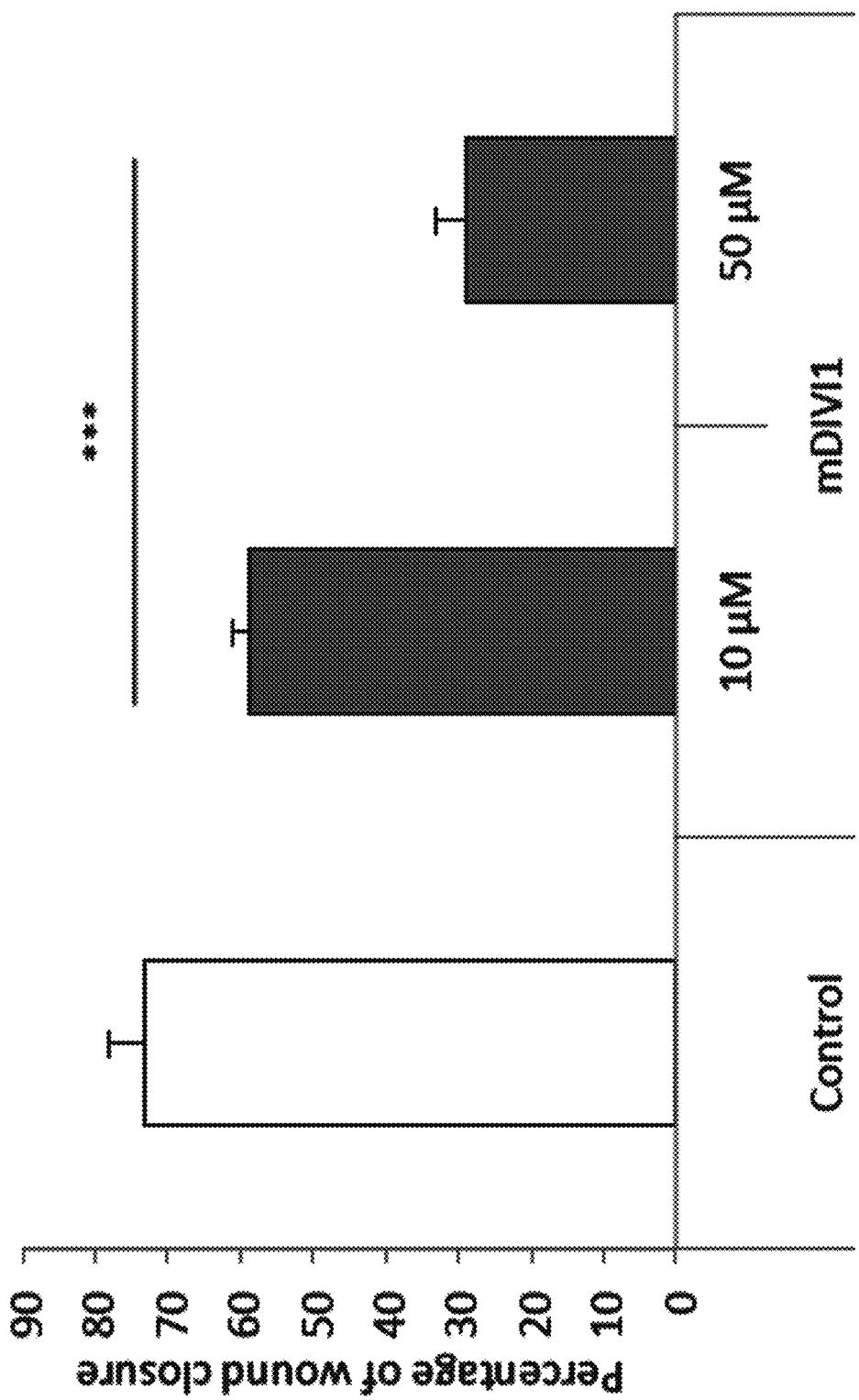

One of the gold standard techniques for the study and identification of CSCs is the sphere formation assay, an in vitro culture system that enriches for CSCs. Under these anchorage-independent culture conditions, CSCs preferentially form the so-called tumorspheres, whereas more differentiated cells die rapidly. Hence, MCF7 cells were grown in suspension as tumorspheres and treated with either vehicle or mDIVI-1 at increasing concentrations. FIG. 7A shows data for tumorsphere growing capacity in MCF7 breast CSCs, A375 melanoma cells, and A549 lung cancer cells, as difference concentrations of mDIVI-1. Five days of exposure to mDIVI-1 decreased MCF7 breast tumorsphere number by 50% at a concentration of 10 μM by 80% at 50 μM and 95% at 100 μM compared to vehicle treated cells. Likewise, A375 melanoma and A549 lung tumorsphere forming capacity were significantly diminished after treatment with mDIVI-1, again in a dose-dependent fashion (by over 35% and 15% at a concentration of 10 μM and by over 90% and 80% at 50 μM, respectively). Inhibition of DRP1 with mDIVI-1 seemed to not only decrease tumorsphere number but also tumorsphere size, as can be seen in the images reproduced as FIG. 7B. Thus, mDIVI-1 inhibited tumorsphere formation in a dose-dependent manner not only in the breast cancer cell line MCF7, but also in melanoma (A375) and lung cancer (A549) cell lines.

with high-energy demand. In migrating cancer cells mitochondria accumulate at the leading edge where processes requiring high energy occur, such as formation of focal adhesions. Fission seems to be a prerequisite for that efficient relocation of mitochondria. Indeed, upregulation/activation of DRP1 is associated with a migratory and invasive phenotype in cancer. Thus, the inventors demonstrated how inducing inhibition of DRP1 through mDIVI-1 treatment decreases the migration of MCF7. Through a scratch assay, were cells were cultured in the presence of either vehicle or mDIVI-1. The scratch was monitored over time and the percentage of wound closure was measured as described previously. FIG. 8A shows images of the scratch assay, for a control, and concentrations of 10 μM and 50 μM mDIVI-1 treatments. The data summarized in FIG. 8B shows that exposure to 10 and 50 μM mDIVI-1 significantly reduced the percentage of wound closure compared to vehicle-treated cells on a 14% and 44% respectively, therefore indicating a clear mDIVI-1-induced dose-dependent reduction in MCF7 cell migration.

TABLE 3

Toxicity effects of differentially expressed proteins and biological functions affected by mDIVI-1 treatment compared to vehicle-treated MCF7 cells

| Categories | Biological functions | p-Value | Activation z-score |
|---|---|---|---|
| Cellular movement | Invasion of cells | 0.00000127 | −1.806 |
| | Invasion of tumour cell lines | 0.00000205 | −1.652 |
| | Cell movement of tumour cell lines | 0.0000138 | −1.628 |
| | Cell movement | 0.0000841 | −1.295 |
| | Migration of tumour cell lines | 0.000153 | −1.164 |
| | Cell movement of breast cancer cell lines | 0.000655 | −1.968 |
| Cell Cycle, Cellular Movement | Cytokinesis | 0.0000132 | −0.669 |
| Cell Cycle, DNA Replication, Recombination, and Repair | Recombination of cells | 0.0000153 | −1.732 |
| | Homologous recombination of cells | 0.0000327 | −1.732 |
| | Homologous recombination | 0.000264 | −1.387 |
| Cell Cycle | Cell cycle progression | 0.000218 | −1.762 |
| Cell Morphology, Cellular Function and Maintenance, DNA Replication, Recombination, and Repair | Repair of cells | 0.00145 | 1.921 |
| | Double-stranded DNA break repair of cells | 0.0035 | 2.069 |
| Cell Morphology | Shape change of tumour cell lines | 0.00354 | −1.446 |
| | Cell spreading | 0.00383 | −1.633 |
| Cellular Assembly and Organization | Formation of cytoskeleton | 0.000722 | 1.95 |
| | Formation of nucleus | 0.00185 | −2 |
| Cellular Function and Maintenance | Endocytosis | 0.000264 | −1.832 |
| Cellular Assembly and Organization | Formation of cytoskeleton | 0.000722 | 1.95 |
| Gene Expression DNA Replication, Recombination, and Repair | Transcription | 0.000829 | 1.993 |
| | Double-stranded DNA break repair | 0.000932 | 2.123 |
| Cell Death and Survival | Cell viability | 0.00417 | −2.813 |

| Ingenuity Toxicity Lists | -log(p-value) | Ratio |
|---|---|---|
| Cholesterol Biosynthesis | 3.12 | 0.312 |
| Fatty Acid Metabolism | 3.02 | 0.133 |
| Decreases Permeability Transition of Mitochondria and Mitochondrial Membrane | 2.46 | 0.429 |

MDIVI-1 Inhibits Migration of MCF7 Cells

It is though that CSCs are responsible for metastatic spread and growth. Emerging evidence highlights the role of mitochondrial dynamics in tumor cell dissemination. These studies suggest that mitochondria are transferred to sites In addition, amongst the altered pathways identified by IPA in the cells treated with mDIVI-1, there were pathways involved in cell motility such as actin cytoskeleton signaling, regulation of actin-based motility by rho, regulation of cellular mechanics by calpain protease (clearly predicted to be inactivated), cdc42 or RhoA signaling, and PAK signaling (see Table 2, above). Likewise, some of the biological functions identified by IPA as affected by mDIVI-1 involved cellular movement, migration and invasion, which in most cases was predicted to be decreased. Data for these biological functions are set forth in Table 3 above.

MDIVI-1 Inhibits Signalling Pathways Required for CSC Survival in MCF7 Cells

Figure 9:
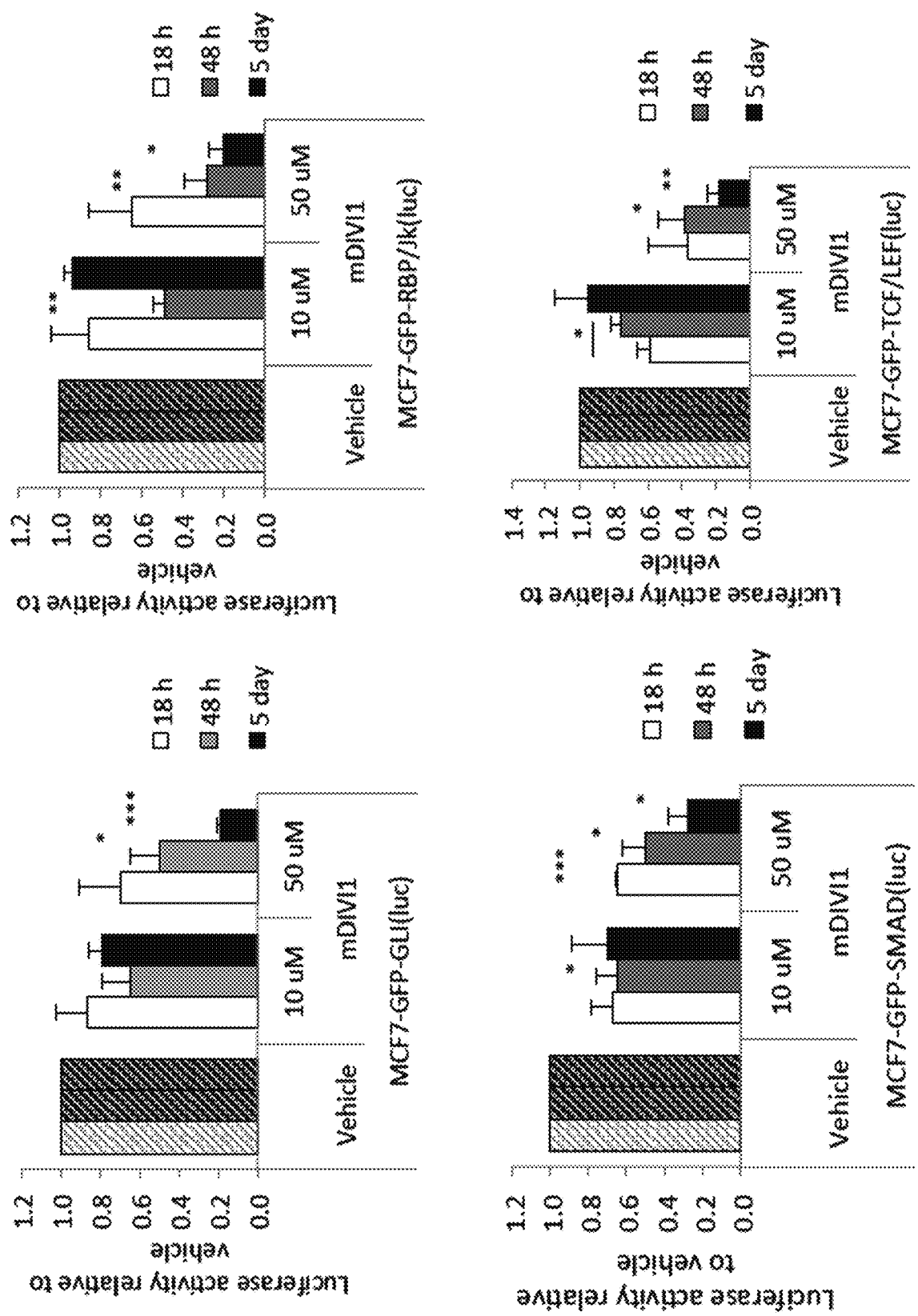
FIG. 9 summarizes data for the impact of mDIVI-1 treatment on various stem-related signaling in MCF7 cells.

Mitochondrial fusion and fission may also have an impact in signaling pathways that regulate stem cell proliferation and survival. The inventors demonstrated how mDIVI-1 exposure affects signaling pathways that regulate stemness. A range of reporter MCF7-GFP cell lines were generated, including MCF7-GFP-GLI(luc), MCF7-GFP-Rbp/Jk(luc), MCF7-GFP-SMAD(luc) and MCF7-GFP-TCF/LEF(luc), to assess Hedgehog signaling, Notch signaling, TGFβ signaling, and Wnt signaling, respectively. These cell lines were exposed to either mDIVI-1 or vehicle and assessed for luciferase activity. The inventors demonstrated that mDIVI-1 treatment significantly inhibited all stem-related signaling pathways in a dose-dependent manner at most of the time points evaluated. The data is shown in the four data plots in FIG. 9. Particularly, 50 μM mDIVI-1 strikingly caused the inhibition of the Hedgehog/GLI pathway, the Notch/Rbp pathway, the Wnt/TCF pathway and the TGFβ/SMAD pathway 2 and 5 days after the start of the treatment.

Moreover, STAT3 (−1.83), EphA2 (−1.74) and BMP7 (−47.17), all proteins involved in signaling pathways associated with cancer stem cell activities, were also found to be down-regulated in the proteomics datasets. Ephrin receptor signaling was specifically found to be significantly altered in MCF7 cells treated with mDIVI-1, compared to vehicle, with a negative z score indicating a slight inhibition of this pathway (see Table 2, above). Likewise, TGFβ was identified by IPA as an upstream regulator predicted to be down-regulated (z score=−1.934).

In summary, mDIVI-1 inhibits all studied signaling pathways related with stemness in MCF7 cancer cells, confirming a suppression of the stem-like phenotype in these cells after treatment.

Figure 10A:
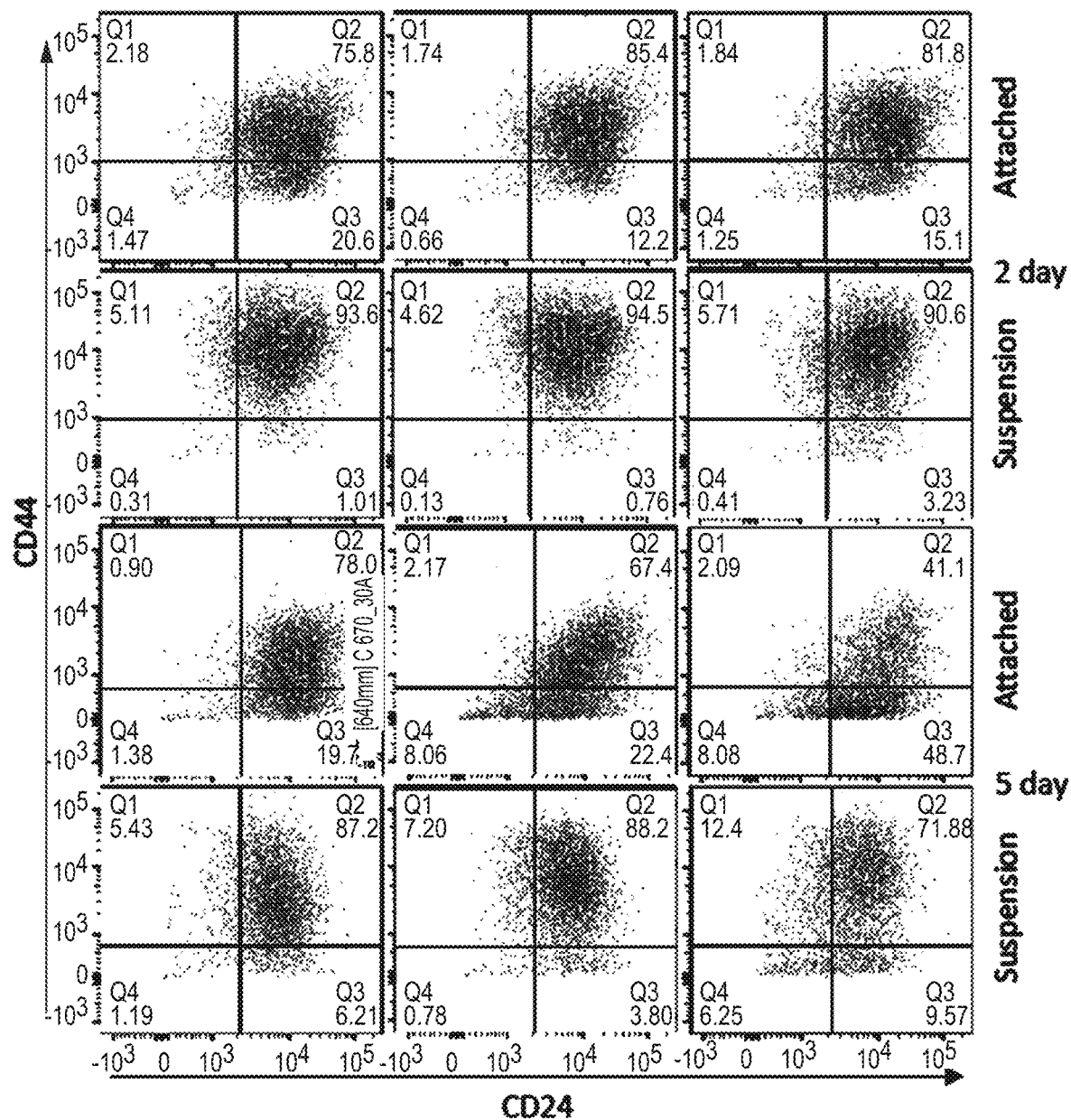
FIG. 10A is a collection of representative graphs showing CD24/CD44 staining of MCF7 cells treated with either vehicle or mDIVI-1.
Figure 10B:
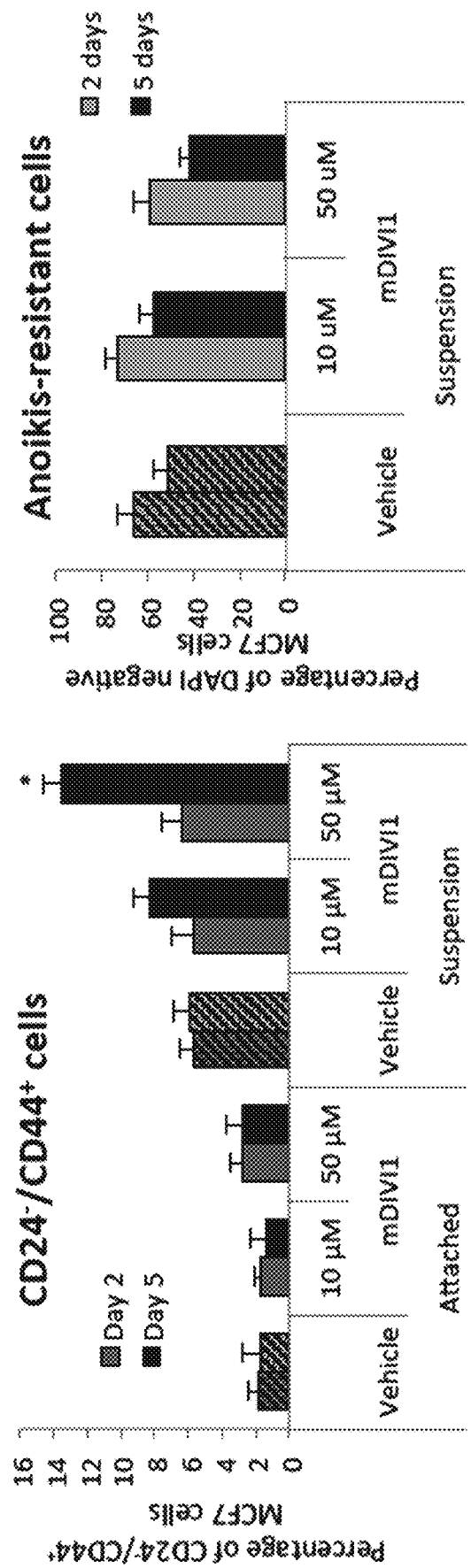
FIG. 10B summarize changes in subpopulations from mDIVI-1 treatment.
Figure 10C:
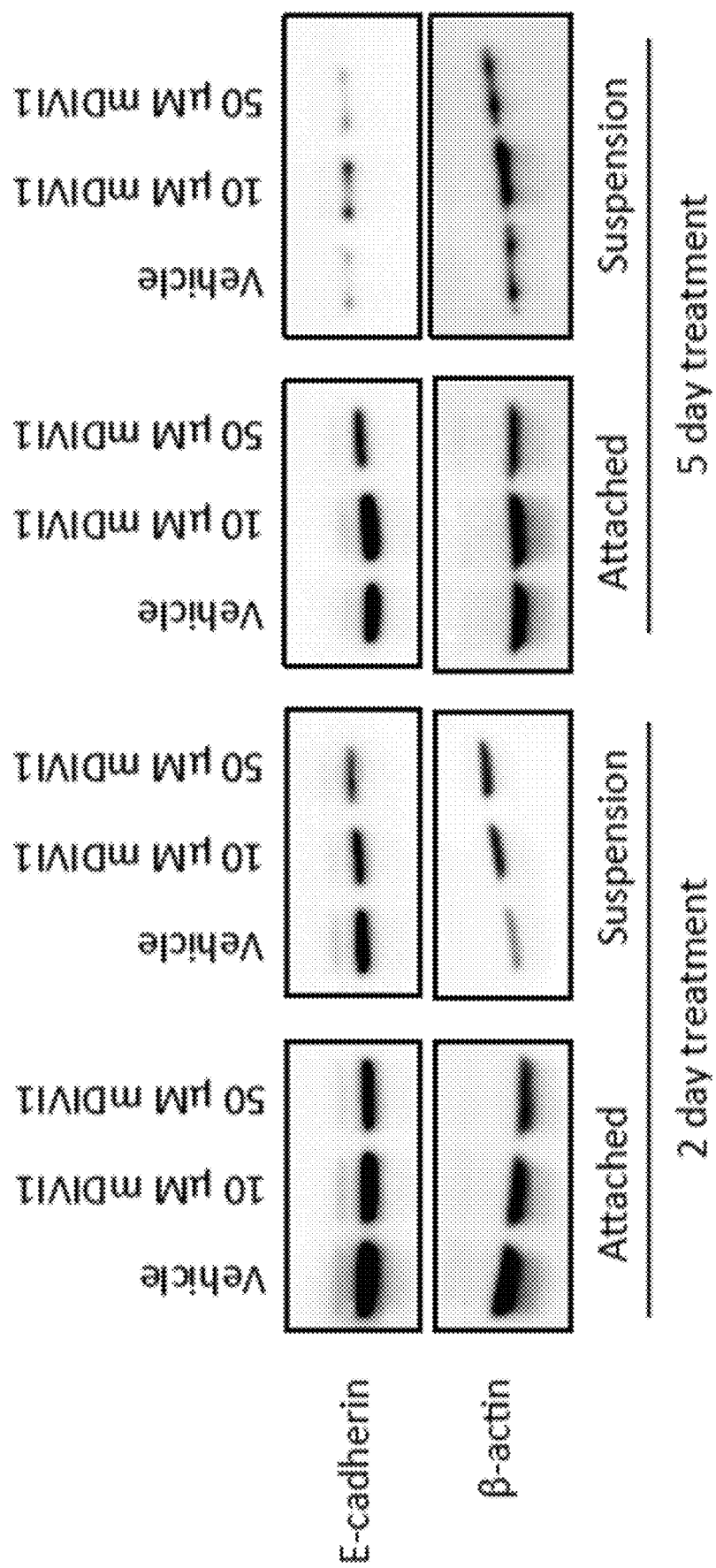
FIG. 10C shows the results of immunoblot analysis of MCF7 cells treated with mDIVI-1.

MDIVI-1 Increases CD44$^+$/CD24$^-$ Population of MCF7 Cells at High Concentrations In human breast cancers, CSCs were first identified by the profile of expression of the cell surface marker CD24$^-$/CD44$^+$. The expression levels of these CSC markers in MCF7, grown either as monolayers or under anchorage-independent conditions, and exposed to mDIVI-1 or vehicle, were the subject of additional analysis. The abundance of the CD24$^-$/CD44$^+$ subpopulation of MCF7 cells was not reduced after exposure to 10 or 50 μM mDIVI-1, compared to vehicle in cells grown as monolayers. FIG. 10A is a representative graph showing CD24/CD44 staining of MCF7 cells treated with either vehicle or mDIVI-1 and grown as either monolayers or in suspension for 2 or 5 days. FIG. 10B shows changes in cell subpopulation. FIG. 10C is an immunoblot analysis of MCF7 cells treated with mDIVI-1 revealed a decrease of E-cadherin expression after mDIVI-1 treatments Moreover, treatment of MCF7 cells in suspension with mDIVI-1 unexpectedly increased the amount of CD24$^-$/CD44$^+$ cells in a dose-dependent fashion. This is evident in FIGS. 10A and 10B. Thus, mDIVI-1 exposure does not alter the proportion of CD24$^-$/CD44$^+$MCF7 CSCs grown as monolayers. However, under anchorage-independent growth conditions, the quantity of CD24$^-$/CD44$^+$MCF7 cells increases in the mDIVI-1 treatments in a dose-dependent manner.

Breast cancer stem cells can exist in distinct states, an mesenchymal-like state and an epithelial-like state, being the first one characterized for its expression of CD24$^-$/CD44$^+$, with an mesenchymal-like gene-expression profile and primarily quiescent. The increase in CD24$^-$/CD44$^+$ MCF7 cells in suspension after treatment with mDIVI-1 should respond to a change in these cells from an epithelial towards a more mesenchymal phenotype. The inventors identified the expression of epithelial markers in MCF7 cells treated with either vehicle or mDIVI-1. Immunoblot analysis of MCF7 cells treated with mDIVI-1 revealed a reduction in the expression of E-cadherin after mDIVI-1 treatment. Decrease in the expression of other epithelial markers was observed also in the proteomics datasets, including EPCAM (−1.58), ZO-1 (−1.62), keratins 8 and 18 (−5.24 and −12.21), CELSR2, involved in loss of polarization (−1.6), F11 receptor (−1.70), junction plakoglobin (−1.65) and desmoplakin (−4.58), although other epithelial markers such as collagen type IV was found to be upregulated by 1.9 fold. However, no mesencymal markers were identified as upregulated by proteomics. Notably, amongst the altered pathways identified by IPA in the mDIVI-1-treated cells were pathways involved in cell to cell interaction and cell junctions such as remodeling of epithelial adherens junctions or epithelial adherens junctions signaling, tight junction signaling, gap junction signaling or FAK, integrin or paxillin signaling (see Table 2, above). Thus, mDIVI-1 exposure induces the acquisition of a CD24$^-$/CD44$^+$ phenotype in MCF7 cells in suspension with loss of epithelial markers, although no complete epithelial-to-mesenchymal transition was observed in the laboratory.

The DAPI staining that was performed in parallel to CD24$^-$/CD44$^+$ staining to be used as quantification of viable cells, also revealed that there were no significant differences in cell viability between vehicle-treated cells and cells treated with mDIVI-1 under anchorage-independent conditions. The second chart in FIG. 10B sets forth the results. That is, mDIVI-1-treated cells are not propagating as efficiently as vehicle-treated cells do, as observed in the tumor-sphere formation assay, however they are more viable after mDIVI-1 treatment in suspension than under attachment conditions. One possible explanation to that observed behavior is that they are becoming more quiescent. In fact, IPA analysis identifies cell cycle, M phase, cytokinesis, cell viability or cell proliferation as biological functions that are predicted to be decreased in MCF7 cells treated with mDIVI-1, compared to vehicle (see Table 3). In addition, treatment with 50 μM mDIVI-1 showed frequent aberrations associated with failure of cytokinesis, which could be seen by DAPI simmunofluorescence staining as an increase in binucleated cells (data not shown). Such phenomenon is typical of anti-mitotic drugs.

Mitochondrial morphology and function contribute to a stem-like phenotype, implying that mitochondrial fission and fusion are central players in CSC behavior. The balance in mitochondrial dynamics is controlled by a small cohort of regulators, such as DRP1. MDIVI-1 is a small molecule inhibitor of DRP1, and as discussed above may be used for inhibiting mitochondrial fission. Emerging evidence demonstrates the implication of mitochondrial fission, and in particular DRP1, in the tumorigenicity and maintenance of stem-like cells. The discussion above demonstrates that mDIVI-1, through inhibition of mitochondrial fission, induces loss of oxidative phosphorylation, therefore reducing the propagation of CSCs, including energetic CSCs, circulating tumor cells, and therapy-resistant cancer cells, as such cell phenotypes rely on their mitochondrial metabolism for their survival.

The results discussed above show that mDIVI-1-induced inhibition of DRP1 in MCF7 cells has a positive effect on mitochondrial mass and production of mitochondrial reactive oxygen species, which in turn has a negative impact on mitochondrial metabolism. Mitochondrial fission plays a role in mitophagy, as it facilitates the elimination of defective organelles via isolation of selective parts of the mitochondria from the mitochondrial network. This explains why, after inhibiting DRP1, a slight increase in mitochondrial mass is observed. A few studies associate DRP1 and mitochondrial oxidative stress. Mitochondrial ROS levels are lower in DRP-overexpressing cells whereas those in a DRP1 mutant that inhibits mitochondrial fission are increased. Moreover, when stress-induced hyperfusion of mitochondria happens in differentiated tissue, it increases mitochondrial ROS levels. MDIVI-1 also causes mitochondrial dysfunction and subsequent cell apoptosis in a DRP1-dependent manner in chemoresistant breast cancer cells. In the current study, mDIVI-1-induced DRP1 inhibition alters the exctracellular acidification rate and oxygen consumption rate of MCF7 cells, transforming them in less aerobic, less metabolically active cells. MDIVI-1 treatment also has a significant impact on lipid metabolism.

The inventors' prior work strongly indicated that mitochondrial function has an implication in the propagation of CSCs. This disclosure shows that mDIVI-1-induced reduction in the respiration of MCF7 cells also impedes their propagation under anchorage-independent conditions. In addition, this disclosure shows that mDIVI-1 treatment decreases tumorsphere forming capacity in melanoma and lung cancer cell lines. The inventors used various approaches to assess CSC phenotype and activity, to account for: (1) individual spheres in the sphere assay can be formed out of aggregation of cells rather than be generated through clonal expansion, and (2) more differentiated cells can also exhibit sphere-forming capability. Also, because tumorspheres themselves are heterogeneous, experiments using them should be interpreted as studies of mixed cell populations enriched for stem-like cells, not totally purified CSCs. The present approach accounted for these considerations by assessing several stemness-related pathways and the migratory ability of mDIVI-1-treated MCF7 cells. Indeed, via generation of several reporter cell lines, the results summarized above confirmed that mDIVI-1 treatment inhibits stemness-related signaling in MCF7, and that mDIVI-1 has a negative effect on MCF7 cell motility.

Increased cell motility and invasion require mitochondrial elongation and trafficking to the periphery of the cell. Several reports link mitochondrial localization and cell motility by describing a redistribution of mitochondria toward the leading edge of cells during persistent migration. DRP1 silencing inhibits lamellipodia formation, a key step for cancer metastasis, by suppressing recruitment of mitochondria to those regions, and therefore decreasing the metastatic potential of breast cancer. In order to be transported around the cells, mitochondria need to be transformed into small units, free from a tight network organization. DRP1 plays a role during that process. Mitochondria might be needed at the leading edge as a source of energy, for calcium signaling, for the stabilization of microtubules by ATP or even for the production of fatty acids and eicosanoids for membrane dynamics in the proximity of focal adhesions. The results summarized above show that treatment with mDIVI-1 alters these processes, including oxidative phosphorylation and ATP production, lipid metabolism, and calcium and focal adhesion signaling (see, e.g., Table 2). Oxidative phosphorylation is actually required for the transfer of mitochondria to the cortical cytoskeleton. In respiration-deficient tumor cells, there is a lack of mitochondria in focal adhesion complexes, and invasion is impaired. Thus, via inhibition of mitochondrial fission and oxidative phosphorylation, mDIVI-1 avoids distribution of mitochondria to the leading edge of the cell, and migration is impeded.

Actin polymerization promotes mitochondrial fission. In addition, actin-depolymerizing drugs inhibit the recruitment of DRP1 to mitochondria and mitochondrial length is reduced. The inventors' proteomics results also show that one of the top canonical pathways affected by mDIVI-1 is the actin cytoskeleton signaling.

Unexpectedly, the results summarized above included an increase in the abundance of $CD24^-/CD44^+$ cells, which is a marker of CSC activity. Breast CSCs can exist in reversible heterogeneous states, a more epithelial-like state, and a more mesenchymal-like state, characterized for its expression of $CD24^-/CD44^+$, with marked reduction of oxygen consumption and increased quiescence. However, although there was a clear reduction of epithelial markers after exposure to mDIVI-1, as well as a reduction of mitochondrial respiration, no mesenchymal markers in MCF7 cells treated with mDIVI-1 could be identified. Interestingly, during pluripotency reprogramming, epithelial-like cells display more fragmented mitochondria, indicating that mitochondrial fission is critical for the acquisition of pluripotency.

Compared to vehicle-treated cells, cells treated with mDIVI-1 seem to survive more in suspension than under attachment conditions, which could be related to the acquisition of a quiescent state. An exhaustive analysis of the cell cycle would be strongly advised to be able to tell whether these cells are actually acquiring a quiescent phenotype or are undergoing senescence. Our proteomics datasets did not identify many markers of senescence. Only LAMP1 was found to be upregulated in cells treated with mDIVI-1 compared to vehicle (2.83), although it is also involved in the processes of autophagy and mitophagy.

In summary, mDIVI-1 has a negative impact on the anchorage-independent growth of MCF7 cells, on their migratory capacity and their signaling pathways related to stemness. However, it seems that mDIVI-1 selects for a phenotype with loss of epithelial markers and features, such as cell to cell contact establishment, and in suspension enriches the $CD24^-/CD44^+$ population of cells. There are multiple explanations for this behavior. First, $CD24^-/CD44^+$ expression may not be representative of CSC activity in this scenario of mitochondrial fission inhibition, as for instance DRP1 effects on CSC behaviour are downstream of CD44, or mDIVI-1 has a direct effect in CD24 loss or CD44 acquisition that does not have an impact on CSC survival. Alternatively, MCF7 cells may enrich their $CD24^-/CD44^+$ expression profile to counteract mDIVI-1 effects, without being able to reverse the inhibition of the CSCs phenotype (tumorsphere formation efficiency, migration and stemness signaling) and therefore depleting CSCs.

Metabolism is materializing as a promising area for cancer treatment. Nevertheless, the notion of targeting cancer mitochondrial metabolism or organelle-driven adaptation is still underdeveloped. The present approach demonstrates the use of metabolism as a pathway for cancer treatment. A better understanding of processes engaged in the regulation of mitochondrial dynamics and their significance for CSC maintenance and propagation will provide instruments to eventually alter them, offering new possible therapeutic approaches. CSCs have adopted metabolic control mechanisms to increase their survival and proliferation. Under the present approach, mitochondrially-targeted drugs may represent promising new agents to interfere with tumor adaptation, ultimately eliminating CSCs. The fact that mDIVI-1 acts as a cytoprotective agent in non-tumor cells and that it would allow a reversible manipulation of mitochondrial morphology highlights its importance as a putative anti-cancer agent.

The therapeutic benefits of mDIVI-1 derivatives is not limited to eradicating CSCs. MDIVI-1 compounds according to the present approach may be used as anti-cancer therapeutics, as well as to target bacteria and pathogenic yeast, provide anti-aging benefits, function as radiosensitizers and/or photo-sensitizers, and/or sensitize bulk cancer cells and cancer stem cells to chemotherapeutic agents, pharmaceuticals, and/or other natural substances. For example, the chemically modified therapeutic agent may also have enhanced anti-viral activity, enhanced anti-bacterial activity, and/or enhanced anti-microbial activity. Thus, embodiments of the present approach may also be used for targeting virus replication, preventing or reducing the growth of pathogenic bacteria, yeast, and parasites, overcoming drug resistance in bacteria (e.g., methicillin-resistant Staph. Aureus, or MRSA).

The therapeutics may be used in the form of pharmaceutical compositions which may be prepared using one or more known methods. For example, a pharmaceutical composition may be prepared by using diluents or excipients such as, for example, one or more fillers, bulking agents, binders, wetting agents, disintegrating agents, surface active agents, lubricants, and the like as are known in the art. Various types of administration unit forms can be selected depending on the therapeutic purpose(s). Examples of forms for pharmaceutical compositions include, but are not limited to, tablets, pills, powders, liquids, suspensions, emulsions, granules, capsules, suppositories, injection preparations (solutions and suspensions), topical creams, and other forms as may be known in the art. For the purpose of shaping a pharmaceutical composition in the form of tablets, any excipients which are known may be used, for example carriers such as lactose, white sugar, sodium chloride, glucose, urea, starch, calcium carbonate, kaolin, cyclodextrins, crystalline cellulose, silicic acid and the like; binders such as water, ethanol, propanol, simple syrup, glucose solutions, starch solutions, gelatin solutions, carboxymethyl cellulose, shelac, methyl cellulose, potassium phosphate, polyvinylpyrrolidone, etc. Additionally, disintegrating agents such as dried starch, sodium alginate, agar powder, laminalia powder, sodium hydrogen carbonate, calcium carbonate, fatty acid esters of polyoxyethylene sorbitan, sodium laurylsulfate, monoglyceride of stearic acid, starch, lactose, etc., may be used. Disintegration inhibitors such as white sugar, stearin, coconut butter, hydrogenated oils; absorption accelerators such as quaternary ammonium base, sodium laurylsulfate, etc., may be used. Wetting agents such as glycerin, starch, and others known in the art may be used. Adsorbing agents such as, for example, starch, lactose, kaolin, bentonite, colloidal silicic acid, etc., may be used. Lubricants such as purified talc, stearates, boric acid powder, polyethylene glycol, etc., may be used. If tablets are desired, they can be further coated with the usual coating materials to make the tablets as sugar coated tablets, gelatin film coated tablets, tablets coated with enteric coatings, tablets coated with films, double layered tablets, and multi-layered tablets. Pharmaceutical compositions adapted for topical administration may be formulated as ointments, creams, suspensions, lotions, powders, solutions, pastes, gels, foams, sprays, aerosols, or oils. Such pharmaceutical compositions may include conventional additives which include, but are not limited to, preservatives, solvents to assist drug penetration, co-solvents, emollients, propellants, viscosity modifying agents (gelling agents), surfactants, and carriers.

The present approach may be used to treat and/or prevent tumor recurrence, metastasis, drug resistance, and/or radiotherapy resistance. Anti-cancer treatments often fail because the tumor recurs or metastasizes, particularly after surgery. Also, drug resistance and radiotherapy resistance are common reasons for cancer treatment failure. It is believed that CSC mitochondrial activity may be, at least in part, responsible for these causes of treatment failure. Embodiments of the present approach may be used in situations where conventional cancer therapies fail, and/or in conjunction with anti-cancer treatments to prevent failure due to tumor recurrence, metastasis, chemotherapy resistance, drug resistance, and/or radiotherapy resistance.

Derivatives of mDIVI-1 may also be used to reverse drug resistance in cancer cells. Drug resistance is thought to be based, at least in part, on increased mitochondrial function in cancer cells. In particular, cancer cells demonstrating resistance to endocrine therapies, such as tamoxifen, are expected to have increased mitochondrial function. MDIVI-1 derivatives inhibit mitochondrial function, and therefore are useful in reducing and, in some cases reversing, drug resistance in cancer cells. Additionally, inhibitors of mitochondrial function may also be used to target bacteria and pathogenic yeast, provide anti-aging benefits, function as radiosensitizers and/or photo-sensitizers, sensitize bulk cancer cells and cancer stem cells to chemotherapeutic agents, pharmaceuticals, and/or other natural substances, such as dietary supplements and caloric restriction.

MDIVI-1 derivatives also have senolytic effects. Regarding anti-aging benefits, senescent cells are toxic to the body's normal healthy eco-system. MDIVI-1 derivatives may be used to selectively kill senescent cells while sparing normal tissue cells. Selectively killing senescent cells may: 1) prevent aging-associated inflammation by preventing acquisition of a senescence-associated secretory phenotype (SASP), which turns senescent fibroblasts into proinflammatory cells that have the ability to promote tumor progression; 2) facilitate tissue repair and regeneration; and/or 3) increase organismal life-span and health-span. These agents may also be used to selectively kill senescent cancer cells that undergo oncogene-induced senescence because of the onset of oncogenic stress.

The present approach provides methods of selectively targeting cancer cells. Bulk cancer cells are largely non-tumorigenic, and while treatments that address bulk cancer cells may provide some therapeutic effect, the majority of deaths due to cancer result from one or more of tumor recurrence, metastasis, drug (e.g., chemotherapy) resistance, and other therapy resistance (e.g., radiotherapy resistance). Certain cell phenotypes are primarily responsible for those conditions, highlighting the importance of eradicating more than mere bulk cells. Unlike conventional therapies, the present approach beneficially targets those cell phenotypes. The target cancer cell may be at least one of a CSC, an energetic cancer stem cell (e-CSC), a circulating tumor cell (CTC, a seed cell leading to the subsequent growth of additional tumors in distant organs, a mechanism responsible for a large fraction of cancer-related deaths), and a therapy-resistant cancer cell (TRCC, a cell that has developed a resistance to one or more of chemotherapies, radiotherapies, and other common cancer treatments).

As described in Applicant's co-pending U.S. Provisional Patent Application Nos. 62/686,881, filed Jun. 19, 2018, and 62/731,561, filed Sep. 14, 2018, and incorporated by reference in their entirety, e-CSCs represent a CSC phenotype associated with proliferation. In addition to bulk cancer cells and CSCs, it should be appreciated that the present approach may be used to target a hyper-proliferative cell sub-population that the inventors refer to as e-CSCs, which show progressive increases in stemness markers (ALDH activity and mammosphere-forming activity), highly elevated mitochondrial mass, and increased glycolytic and mitochondrial activity. Derivatives of mDIVI-1 induce mitochondrial dysfunction and repress mitochondrial metabolism, effects that are amplified in hyper-proliferative e-CSCs.

In view of the foregoing, it should be appreciated that the present approach may take a wide variety of forms, depending on the embodiment. For example, embodiments of the present approach may take the form of a composition, such as a pharmaceutical composition. The therapeutic compound may be the active ingredient, and may be present in a pharmaceutically-effective amount.

An mDIVI-1 derivative may be chemically modified with one or more mitochondria-targeting compounds, to improve the selectivity and uptake of the therapeutic agent. The mitochondria-targeting compound may be, for example, at least one of palmitic acid, stearic acid, myristic acid, oleic acid, a short-chain fatty acid, a medium-chain fatty acid, tri-phenyl-phosphonium (TPP), and a TPP-derivative. For example, the mitochondria-targeting compound may be a TPP-derivative being at least one of 2-butene-1,4-bis-TPP; 2-chlorobenzyl-TPP; 3-methylbenzyl-TPP; 2,4-dichlorobenzyl-TPP; 1-naphthylmethyl-TPP; p-xylylenebis-TPP; a derivative of 2-butene-1,4-bis-TPP; a derivative of 2-chlorobenzyl-TPP; a derivative of 3-methylbenzyl-TPP; a derivative of 2,4-dichlorobenzyl-TPP; a derivative of 1-naphthylmethyl-TPP; and a derivative of p-xylylenebis-TPP. The targeting compound may also be another lipophilic cation, such as 10-nonylacridine orange bromide.

Embodiments of the present approach may possesses anti-cancer activity. In some embodiments, the composition possesses at least one of radiosensitizing activity and photosensitizing activity. In some embodiments, the composition sensitizes cancer cells to at least one of chemotherapeutic agents, natural substances, and caloric restriction. In some embodiments, the composition selectively kills senescent cells. In some embodiments, the composition prevents acquisition of a senescence-associated secretory phenotype. In some embodiments, the composition facilitates tissue repair and regeneration. In some embodiments, the composition increases at least one of organismal life-span and health-span.

Embodiments of the present approach may also take the form of methods for preventing at least one of tumor recurrence, metastasis, drug resistance, and radiotherapy resistance. In some embodiments, an effective amount of a composition having, as its active ingredient, a therapeutic compound having an mDIVI-1 derivative may be administered. In some embodiments, the mDIVI-1 derivative may be chemically modified with at least one of palmitic acid, stearic acid, myristic acid, oleic acid, a short-chain fatty acid, a medium-chain fatty acid, 10-N-nonyl acridine orange tri-phenyl-phosphonium (TPP), and a TPP-derivative, may be administered.

The present approach may also take the form of methods for targeting a therapeutic compound to a cancer cell mitochondria. The therapeutic compound may be chemically modified with a mitochondria-targeting compound, such as, for example, at least one of palmitic acid, stearic acid, myristic acid, oleic acid, a short-chain fatty acid, a medium-chain fatty acid, tri-phenyl-phosphonium (TPP), and a TPP-derivative. The cancer cell may be, for example, at least one of a cancer stem cell, an energetic cancer stem cell (as described herein), a circulating tumor cell, and a therapy-resistant cancer cell. The chemically modified therapeutic agent may have, in some embodiments, at least one of enhanced anti-viral activity, enhanced anti-bacterial activity, and enhanced anti-microbial activity.

The following paragraphs provide an overview of assays discussed above.

CELL CULTURE: Human MCF7 breast cancer cells were purchased from ATCC and maintained in complete media: DMEM (D6546, Sigma) supplemented with 10% fetal bovine serum (F7524, Sigma), 100 units/ml of penicillin, 100 µg/ml, streptomycin (P0781, Sigma) and 1% Glutamax (#35050087, Life Technologies). For all experiments, cells were incubated in a 5% $CO_2$ atmosphere at 37° C.

CHEMICALS: MDIVI-1, or 3-(2,4-Dichloro-5-methoxyphenyl) 2,3-dihydro 2-thioxo-4(1H) quinazolinone (sc-215291, Santa Cruz), an inhibitor of mitochondrial division DRP1 and dynamin I, was used in this study at the concentrations indicated. Vehicle-treated cells (DMSO 0.5%) were analysed in all experiments.

PRESTOBLUE VIABILITY ASSAY: Cell viability was measured using the resazurin-based PrestoBlue reagent (A-13261, ThermoFisher Scientific). Briefly, 5×103 MCF7 cells were seeded into 96-well black plates. When cells were attached mDIVI-1 or vehicle were added to the cells. After 2 or 5 days, PrestoBlue reagent was added to the cells and incubated for 2 hours. Plates were finally read using a FluoStar Omega plate reader (BMG Labtech) at an excitation wavelength of 544 and an emission wavelength of 590 nm. Background measurements were subtracted from all values.

MITOCHONDRIAL MASS QUANTIFICATION: To measure mitochondrial mass, cells were stained with MitoTracker Deep Red (M22426, Invitrogen). Briefly, 2×105 hTERT-BJ1 cells per well were seeded in 6-well plates. When cells were attached, mDIVI-1 and vehicle treatments were added for 2 days or 5 days in triplicate. Cells were then incubated for 15 min at 37° C. with the 10 nM Mitotracker Deep Red probe diluted in PBS (D8662, Sigma). All subsequent steps were performed in the dark. Cells were washed in PBS, harvested, and resuspended in PBS. Mitotracker signal was quantified as mean fluorescent intensity of the viable cell population in a Fortessa flow cytometer (BD Bioscience). Results were analyzed using FlowJo software.

MITOCHONDRIAL STAINING: One hundred thousand MCF7 cells were seeded onto coverslips in 12-well plates. When cells were attached, mDIVI-1 and vehicle treatments were performed in triplicate. After 2 days and 5 days, mitochondria were labeled by incubating cells for 15 min at 37° C. with 25 nM of MitoTracker DeepRed (M22426, Invitrogen) diluted in PBS (D8662, Sigma). Then, cells were washed with PBS, fixed in 2% paraformaldehyde (28908, Thermo Scientific) in PBS for 30 minutes at room temperature and mounted with ProLong® Gold Antifade Mountant reagent with DAPI (P36935, Invitrogen, Inc.). Immunofluorescence pictures were taken in a Leica gated Stimulated Emission Depletion Microscopy (gSTED) with additional confocal and multi-photon illumination (room rg106).

LEVELS OF REACTIVE OXYGEN SPECIES AND MITOCHONDRIAL SUPEROXIDE: For both assays, 2×105 MCF7 cells were seeded in 35 mm plates. When cells were attached, either vehicle or mDIVI-1 were added to the cells for 24, 48 hours or 5 days in triplicate. Reactive oxygen species (ROS) production was measured using CM-H2DCFDA (C6827, Invitrogen). Briefly, cells were incubated for 20 minutes at 37° C. with 1 µM CM-H2DCFDA diluted in PBS and then placed in complete media for 20 minutes at 37° C. in the dark, to render the dye fluorescent, according to the manufacturer. Mitochondrial superoxide was measured using MitoSOX Red Mitochondrial Superoxide Indicator (M36008, ThermoFisher Scientific). Briefly, cells were incubated for 10 minutes at 37° C. in the dark with 5 µM MitoSOX diluted in PBS, according to the manufacturer. ROS signal and MitoSOX signal was quantified as mean fluorescent intensity of the viable cell population in a Fortessa flow cytometer (BD Bioscience). Results were analysed using FlowJo software.

EXTRACELLULAR FLUX ANALYSIS AND BRADFORD ASSAY: Extracellular acidification rate (ECAR) and oxygen consumption rate (OCR) were measured in a XF96 Extracellular Flux Analyzer (Seahorse Biosciences). Briefly, 1×104 MCF7 cells per well were seeded in XF96 plates and incubated with complete medium. When cells were attached, mDIVI-1 and vehicle treatments were added. Six replicates were run for each condition. After 48 hours, un-buffered DMEM XF medium supplemented with 2 mM glutamine (pH 7.4) was added to the cells, and placed in a 37° C. CO2-free incubator for 1 hour. Ten mM glucose, 1 µM oligomycin and 100 mM 2-deoxyglucose (2-DG) were injected into the media at different time points and ECAR was measured. Likewise, ECAR and OCR were quantified using un-buffered DMEM XF medium supplemented with 2 mM glutamine, 2 mM sodium pyruvate and 10 mM glucose. One µM oligomycin, 0.9 µM FCCP and 1 µM rotenone and antimycin A were injected into the media at different time points and OCR and ECAR were measured. Cells were finally lysed with 0.1 M NaOH and protein lysate was subsequently stained with Quick Start™ Bradford 1× Dye Reagent (500-0205, BioRad) to normalise results. All parameters were calculated according to manufacturer.

TUMORSPHERE FORMATION ASSAY: A single cell suspension was prepared using enzymatic (1× Trypsin-EDTA, T3924, Sigma Aldrich), and manual disaggregation (25 gauge needle). Cells were plated at a density of 5000 cells/well in tumorsphere media (DMEM-F12/B27/EGF (20 ng/ml)/Pen-Strep) in non-adherent conditions, in 6-well plates coated with (2-hydroxyethylmethacrylate) (poly-HEMA, P3932, Sigma) in the presence of mDIVI-1 or vehicle. After 5 days of culture in a humidified incubator at 37° C., tumorspheres bigger than 50 µm were counted using an eye piece graticule.

SCRATCH ASSAY: A hundred thousand MCF7 cells per well were seeded in 12-well plates. When cells were attached, a horizontal scratch was performed using the tip of a pipette. Immediately after, the media was removed and either fresh vehicle-containing media or mDIVI-1-containing media were added to the cells for 48 hours. Four replicates were used for each condition. Cells were incubated in a 5% CO2 atmosphere at 37° C. in an Incucyte ZOOM System (Essen Bioscence). The wound closure was monitored by taking pictures of each well every 4 hours. At the end of the treatment, pictures of the wells at 0 and 48 hours were analysed using ImageJ software to calculate wound closure according to the following formula: Percentage wound closure=[(wound area0 h−wound area48 h)/wound area0 h]×100.

LUCIFERASE ASSAY: The Cignal Lenti reporter assay (luc) was used to monitor the activity of several signalling pathways in MCF7-GFP cells as explained previously. Luciferase Assay System (E1501, Promega) was performed according to manufacturer's instructions. 1×104 MCF7 fibroblasts were seeded in black-walled 96 well plates. When cells were attached, drug treatments were added for 18, 48 hours and 5 days. After treatment, Luciferase Assay was performed according to manufacturer's instructions and light signal was acquired in the Xenogen VivoVision IVIS Lumina. Results were normalized by SRB staining of cells grown in 96-well plates in parallel.

SULFORHODAMINE B (SRB) ASSAY: SRB (S9012, Sigma) measures total biomass by staining cellular proteins. After treatment, cells were fixed in 10% tricloroacetic acid (T9159, Sigma) for 1 hour at 4° C., stained with SRB (S9012, Sigma) for 15 minutes, and washed 3 times with 1% acetic acid (27225, Sigma). The incorporated die was solubilized with 10 mM Tris Base, pH 8.8 (T1503, Sigma). Absorbance was spectrophotometrically measured at 562 nm in a FluoStar Omega plate reader (BMG Labtech). Background measurements were subtracted from all values.

CD24/CD44 EXPRESSION: Four hundred thousand MCF7 cells were seeded either in either a regular 10 cm dish or in five 15 cm dishes coated with (2-hydroxyethylmethacrylate) (poly-HEMA, P3932, Sigma) in the presence of mDIVI-1 or vehicle for 2 days or 5 days. Following mDIVI-1 treatment, MCF7 cells grown either in suspension or as monolayers were analysed for their expression of CD24 and CD44. The surviving fraction after 2 days and 5 days of growth was analyzed by FACS. MCF7 cells were either trypsinised or spun down and trypsinised and incubated with CD24 (IOTest CD24-PE, Beckman Coulter) and CD44 (APC mouse anti-human CD44, 559942, BD Pharmingen) for 15 minutes on ice. Cells were then rinsed twice in PBS, spun down, and resuspended with DAPI dye (D1306, Molecular probes) at 3 µM in PBS for 10 minutes. Samples were then analyzed by FACS (Fortessa, BD Bioscence). Only the live cell population, identified using the DAPI staining, was analyzed for CD24/CD44 expression. Data were analyzed using FlowJo software. Only those cells expressing CD44 that did not express CD24 were considered to be the CD24−/CD44+ CSC subpopulation.

WESTERN BLOTTING: Two million MCF7 cells were seeded either in regular 15 cm dishes or in five 15 cm dishes coated with (2-hydroxyethylmethacrylate) (poly-HEMA, P3932, Sigma) in the presence of mDIVI-1 or vehicle for 2 days or 5 days. At the end of the treatment, cells in suspension were spun down and lysed and attached cells were directly lysed in RIPA lysis buffer (R0278, Sigma) containing proteinase inhibitors (05 892 970 001, Roche) and kept at 4° C. for 20 minutes with rotation. Lysates were cleared by centrifugation for 10 minutes at 10,000×g and supernatants were collected. Equal amounts of protein lysate, as determined by using the BCA protein assay kit (23225, Pierce) were diluted in SDS sample buffer and dry-boiled for 5 minutes before being separated by SDS-PAGE using 4-20% gels (456-1094, Biorad). Samples were then blotted onto nitrocellulose membranes (170-4159, Biorad), blocked in 5% milk in TBS-Tween 20 (P9416, Sigma) for 1 hour and probed with antibodies against E-cadherin (ab8995, Abcam) or β-actin (a2228, Sigma). Bound antibodies were detected using a horseradish peroxidase-conjugated secondary antibody (ab6789 and ab6721, Abcam) and signal was obtained using Supersignal West Pico chemiluminiscent substrate (34087, ThermoScientific). Pictures were taken in a ChemiDoc XRS with Image Lab Software (BioRad).

LABEL-FREE SEMI-QUANTITATIVE PROTEOMICS: Chemicals and sample preparation. Formic acid, trifluoroacetic acid, ammonium formate (10 M), ammonium bicarbonate TCEP (Tris (2-carboxyethyl)phosphine hydrochloride), MMTS (Methyl methanethiosulfonate) and trypsin were all obtained from Sigma. HPLC gradient grade acetonitrile was obtained from Fisher Scientific. Briefly, 2×106 MCF7 cells were seeded in 15 cm plates until cells were attached. Cells were then treated with 10 μM mDIVI-1. As control, vehicle-treated cells were processed in parallel. After 48 hours of treatment, cells were lysed in RIPA buffer (R0278, Sigma) and kept at 4° C. for 20 minutes with rotation. Lysates were cleared by centrifugation for 10 minutes at 10,000×g and supernatants were collected and kept frozen at −80° C.

PROTEIN DIGESTION: Lysate samples were thawed to room temperature and their concentrations equalized to 1 μg/μL (50 μL volume) with RIPA buffer, and further processed for trypsin digestion by sequential reduction of disulphide bonds with TCEP and alkylation with MMTS. Briefly, 1 μL benzonase (Novagen) was added to the 50 μL aliquot and placed on ice for 15 minutes. The sample was then taken to dryness using a SpeedVac, and resuspended in 22.5 μL trypsin reaction buffer (40 mM ammonium bicarbonate and 9% acetonitrile). One μL of 50 mM TCEP solution was added to each sample, mixed briefly and placed on a heater block at 60° C. for 60 minutes. After cooling to room temperature, 0.5 μL of 200 mM MMTS solution was added to each sample and allowed to react for 15 minutes. Trypsin was added in two waves to ensure efficient digestion of the sample. Firstly, 20 μg of sequencing grade trypsin was resuspended in 1800 μL of trypsin reaction buffer; 225 μL of this solution were added to each sample for digestion, and the reactions were left at 37° C. overnight with shaking (600 rpm). The following morning, a further aliquot of trypsin was added. Two ml of trypsin reaction buffer was added to 20 μL of sequencing grade trypsin; 250 μL of this solution were added to each of the digest samples from overnight, and the reactions were left at 37° C. for 4 hours with shaking (600 rpm). Thirty-five μL 10% formic acid were added to the 500 μL digest sample (0.7% final concentration of formic acid) to stop the digestion. The digested solution was diluted in 7.5 mL of acetonitrile containing 0.3% formic acid.

HILIC solid phase extraction (SPE) of peptides. Polyhydroxyethyl A SPE 12 μm, 300 A, 300 mg cartridges (obtained from PolyLC) were used for the HILIC procedure. Prior to use, cartridges required an overnight soak in 50 mM formic acid followed by rinsing with water the following day. Cartridges were preconditioned with 2 mL of Buffer A (90% acetonitrile, 5 mM ammonium formate, pH 2.7) followed by 2 mL of Buffer B (5 mM ammonium formate, pH 2.7) and finally re-equilibrated with 10 mL Buffer A. The diluted samples were loaded onto the cartridges and washed with a further 10 mL Buffer A. Finally, peptides were eluted in 1 mL Buffer C (9 parts Buffer B plus 1 part Buffer A) and the samples dried on a Speedvac to remove organic solvent prior to LC-MS/MS analysis.

LC-MS/MS analysis. Lyophilised digests were resuspended in 50 μL of 0.1% TFA to give an approximate concentration of 1 μg/μL. One μL injection volumes were used throughout resulting in an on-column peptide loading of approximately 1 μg per injection. Analysis was performed in quintuplicate for each sample. All LC-MS/MS analyses were performed on an LTQ Orbitrap XL mass spectrometer coupled to an Ultimate 3000 RSLCnano system (Thermo Scientific). One μL injection volumes were used throughout and samples loaded directly onto the analytical column, PepMap RSLC C18, 2 μm×75 μm id×50 cm (Thermo Scientific). The composition (v/v) of LC buffers were as follows; Buffer A—99.9% water plus 0.1% formic acid and Buffer B—80% acetonitrile, 19.9% water and 0.1% formic acid. Peptides were loaded directly onto the column at a flow rate of 400 nl/min with an initial mobile phase composition of 1% B. The organic strength was increased linearly from 1% to 22.5% B over 22.5 minutes again at 400 nl/min, followed by an increase to 24.8% B over the next 2.6 minutes with a concomitant reduction in flow rate to 300 nl/min, and to 39% B over a further 14 minutes. A further increase to 60% B over the next 5 minutes was followed by a ramp to 95% B over 2.5 minutes where it was held for a further 2 minutes. The column was then allowed to re-equilibrate to 1% B for a total analysis time of 74 minutes. The mass spectrometer was instructed to perform data dependent acquisition on the top six precursor ions, which were measured in the Orbitrap FTMS detector over the mass range 370-1200 m/z, at a nominal resolution of 60,000. MS/MS spectra were acquired in the ion trap under CID conditions with normalized collision energy of 35, isolation width of 3 Th, Q value of 0.25 and 30 ms activation time. Gas-phase fractionation was performed on the five replicate injections such that MS/MS data was collected for precursor ion range 370-494 m/z Injection 1, 494-595 m/z Injection 2, 595-685 m/z Injection 3, 685-817 m/z Injection 4 and 817-1200 m/z Injection 5.

Statistical Analysis: Xcalibur raw data files acquired on the LTQ-Orbitrap XL were directly imported into Progenesis LCMS software (Waters Corp) for peak detection and alignment. Data were analysed using the Mascot search engine. Five replicates were analysed for each sample type (N=5).

INGENUITY PATHWAY ANALYSES: Pathway and function analyses were generated using Ingenuity Pathway Analysis (IPA) (Ingenuity systems, http://www.ingenuity.com), which assists with proteomics data interpretation via grouping differentially expressed genes or proteins into known functions and pathways. Pathways with a z score>1.9 were considered as significantly activated, and pathways with a z score<−1.9 were considered as significantly inhibited.

STATISTICAL ANALYSES: ANOVA was used for statistical comparison of three or more groups. For normalised data, one-sample t test was performed. All data are reported as mean±standard deviation of the mean (SEM). All experiments were performed at least three times with reproducible results unless otherwise stated. P values lower than 0.05 were considered significant (*P<0.05, P<0.01, *P<0.001). Microsoft Excel was used to produce all graphs except FACS analysis graphs, in which case FlowJo was used.

The terminology used in the description of the invention herein is for the purpose of describing particular embodiments only and is not intended to be limiting of the invention. As used in the description of the invention and the appended claims, the singular forms "a," "an" and "the" are intended to include the plural forms as well, unless the context clearly indicates otherwise. The invention includes numerous alternatives, modifications, and equivalents as will become apparent from consideration of the following detailed description.

It will be understood that although the terms "first," "second," "third," "a)," "b)," and "c)," etc. may be used herein to describe various elements of the invention, and the claims should not be limited by these terms. These terms are only used to distinguish one element of the invention from another. Thus, a first element discussed below could be termed an element aspect, and similarly, a third without departing from the teachings of the present invention. Thus, the terms "first," "second," "third," "a)," "b)," and "c)," etc. are not intended to necessarily convey a sequence or other hierarchy to the associated elements but are used for identification purposes only. The sequence of operations (or steps) is not limited to the order presented in the claims.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the present application and relevant art and should not be interpreted in an idealized or overly formal sense unless expressly so defined herein. The terminology used in the description of the invention herein is for the purpose of describing particular embodiments only and is not intended to be limiting of the invention. All publications, patent applications, patents and other references mentioned herein are incorporated by reference in their entirety. In case of a conflict in terminology, the present specification is controlling.

Also, as used herein, "and/or" refers to and encompasses any and all possible combinations of one or more of the associated listed items, as well as the lack of combinations when interpreted in the alternative ("or").

Terms such as "treating," "treatment," and the like, are used herein to generally refer to achieving a desired pharmacologic and/or physiologic effect. The effect(s) may be prophylactic in terms of completely or partially preventing a disease, and/or the effect(s) may be therapeutic in terms of a partial or complete cure for a disease and/or adverse effect attributable to the disease. "Treatment" as used herein covers any treatment of a disease in a mammal, and includes, for example, preventing the disease from occurring in a subject which may be predisposed to the disease but has not yet been diagnosed as having it; inhibiting the disease, i.e., arresting its development; or relieving the disease, i.e., causing regression of the disease. The therapeutic agent may be administered before, during or after the onset of disease or injury. The treatment of ongoing disease, where the treatment stabilizes or reduces the undesirable clinical symptoms of the patient, is of particular interest.

The term "prevent," and similar words such as "prevented," "preventing," etc., indicate an approach for preventing, inhibiting, and/or reducing the likelihood of the occurrence or recurrence of a disease or condition. Such terms may also refer to delaying the onset or recurrence of a disease or condition or delaying the occurrence or recurrence of the symptoms of a disease or condition. The term "prevention" and similar words also include reducing the intensity, effect, symptoms and/or burden of a disease or condition prior to onset or recurrence of the disease or condition.

As used herein, the phrases "effective amount" and "pharmaceutically effective amount" refer to a quantity, concentration, and/or dosing regimen, of one or more agents, sufficient to achieve a beneficial or desired prophylactic or therapeutic result, including clinical results. It should be appreciated that a pharmaceutically effective amount may be determined through the use of methods available to persons having ordinary skill in the art. It should also be appreciated that a pharmaceutically effective amount may vary according to factors such as the disease state, age, sex, and weight of the individual, as well as the particular agent(s) and/or methodologies, to elicit a desired response in the individual. A therapeutically effective amount may also be one in which any toxic or detrimental effects of the agent are outweighed by the therapeutically beneficial effects. The term "therapeutically effective amount" includes an amount that is effective to "treat" a subject (e.g., a patient).

The terms "promoting," "enhancing," "stimulating," and "increasing," generally refer to the ability of compositions according to the present approach to produce and/or cause a greater physiological response (i.e., measurable downstream effect), as compared to the response caused by either vehicle or a control molecule/composition. One such measurable physiological response includes, without limitation, increased cell killing and/or tumor reduction, increased survival, increased treatment efficacy compared to normal, untreated, or control-treated subjects. The physiological response may be increased by at least 5%, 10%, 20%, 30%, 40%, 50%, 60%, 70%, 80%, 90%, 100%, 125%, 150%, 175%, 200%, or greater, as compared to the response measured in normal, untreated, or control-treated subjects. An "increased" or "enhanced" response or property is typically "statistically significant," and may include an increase that is 1.1, 1.2, 1.5, 2, 3, 4, 5, 6, 7, 8, 9, 10, 15, 20, 30 or more times (e.g., 500, 1000 times) (including all integers and decimal points in between and above 1, e.g., 1.5, 1.6, 1.7. 1.8, etc.) that produced by normal, untreated, or control-treated subjects.

The terms "decrease," "lower," "lessen," and "reduce" generally refer to the ability of compositions according to the present approach to produce and/or cause a lesser physiological response (i.e., a measurable downstream effect), as compared to the response caused by either vehicle or a control molecule/composition, e.g., decreased tumor volume. A "decrease" or "reduced" response is typically a "statistically significant" response, and may include an decrease that is 1.1, 1.2, 1.5, 2, 3, 4, 5, 6, 7, 8, 9, 10, 15, 20, 30, or more times (e.g., 500, 1000 times) (including all integers and decimal points in between and above 1, e.g., 1.5, 1.6, 1.7. 1.8, etc.) the response produced by normal, untreated, or control-treated subject.

The phrase "treatment cycle" refers to a course of treatment, such as a dosing schedule that is repeated on a regular or pre-defined basis. A treatment cycle can comprise several days of treatment followed by several days of rest. For example only, an agent may be administered daily for two weeks, followed by two weeks of no treatment, over a 4-week treatment cycle. It should be appreciated that a treatment cycle may depend on a number of factors, such as the disease state, age, sex, and weight of the individual, as well as the particular agent(s) and/or methodologies, to elicit a desired response in the individual.

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a complex comprises components A, B and C, it is specifically intended that any of A, B or C, or a combination thereof, can be omitted and disclaimed.

As used herein, the transitional phrase "consisting essentially of" (and grammatical variants) is to be interpreted as encompassing the recited materials or steps "and those that

What is claimed is:

1. A compound comprising the general formula:

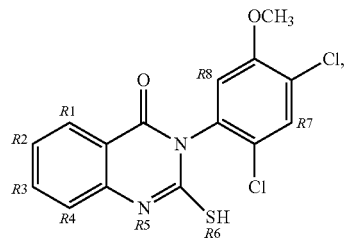

wherein each of R1 through R8 is selected from the group consisting of hydrogen, fluorine, chlorine, bromine, iodine, carboxyl, alkanes, cyclic alkanes, alkenes, cyclic alkenes, alkynes, ketones, aldehydes, carboxylic acids, ethers, esters amines, amides, monocyclic or polycyclic arene, heteroarenes, phenols, benzoic acid, membrane-targeting signal, and a mitochondria-targeting signal; and wherein at least one R-group comprises a targeting signal selected from the group consisting of palmitic acid, stearic acid, myristic acid, and oleic acid.

2. A method of inhibiting cancer stem cell propagation, the method comprising administering to a patient in need thereof a pharmaceutically effective amount of a compound comprising the general formula:

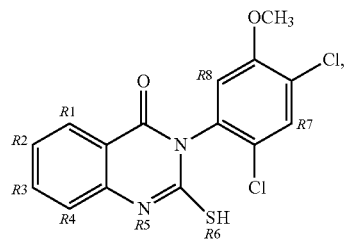

wherein each of R1 through R8 is selected from the group consisting of hydrogen, fluorine, chlorine, bromine, iodine, carboxyl, alkanes, cyclic alkanes, alkenes, cyclic alkenes, alkynes, ketones, aldehydes, carboxylic acids, ethers, esters amines, amides, monocyclic or polycyclic arene, heteroarenes, phenols, benzoic acid, membrane-targeting signal, and a mitochondria-targeting signal, wherein at least one R-group comprises a targeting signal selected from the group consisting of palmitic acid, stearic acid, myristic acid, and oleic acid; and a pharmaceutically acceptable carrier.

3. A method for eradicating cancer stem cells, the method comprising delivering to the cancer stem cells a pharmaceutically effective amount of a compound comprising the general formula:

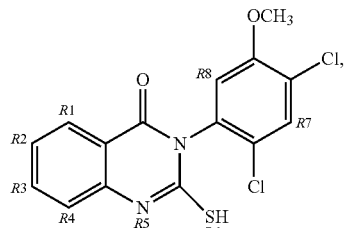

wherein each of R1 through R8 is selected from the group consisting of hydrogen, fluorine, chlorine, bromine, iodine, carboxyl, alkanes, cyclic alkanes, alkenes, cyclic alkenes, alkynes, ketones, aldehydes, carboxylic acids, ethers, esters amines, amides, monocyclic or polycyclic arene, heteroarenes, phenols, benzoic acid, membrane-targeting signal, and a mitochondria-targeting signal, wherein at least one R-group comprises a targeting signal selected from the group consisting of palmitic acid, stearic acid, myristic acid, and oleic acid; and a pharmaceutically acceptable carrier.

4. The method of claim 3, wherein the cancer stem cells comprise at least one of energetic cancer stem cells, circulating tumor cells, and treatment-resistant cancer stem cells.

5. A method for treating at least one of MCF7 tumor recurrence, MCF7 metastasis, drug resistance in MCF7 cells, and radiotherapy resistance in MCF7 cells, the method comprising: administering a pharmaceutically effective amount of a compound comprising the general formula:

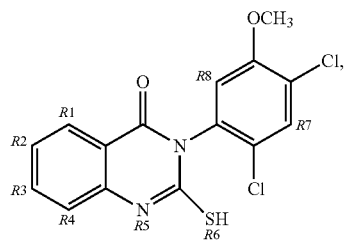

wherein each of R1 through R8 is selected from the group consisting of hydrogen, fluorine, chlorine, bromine, iodine, carboxyl, alkanes, cyclic alkanes, alkenes, cyclic alkenes, alkynes, ketones, aldehydes, carboxylic acids, ethers, esters amines, amides, monocyclic or polycyclic arene, heteroarenes, phenols, benzoic acid, membrane-targeting signal, and a mitochondria-targeting signal; and wherein at least one R-group comprises a targeting signal selected from the group consisting of palmitic acid, stearic acid, myristic acid, and oleic acid.

6. A method of treating at least one of tumor recurrence, metastasis, drug resistance, and radiotherapy resistance, the method comprising administering a compound of claim 1, at least one of prior to a cancer treatment, with a cancer treatment, and following a cancer treatment.

7. A method of preventing at least one of MCF7 tumor recurrence, MCF7 metastasis, drug resistance in MCF7 cells, and radiotherapy resistance in MCF7 cells, the method comprising: administering a pharmaceutically effective amount of a compound comprising the general formula:

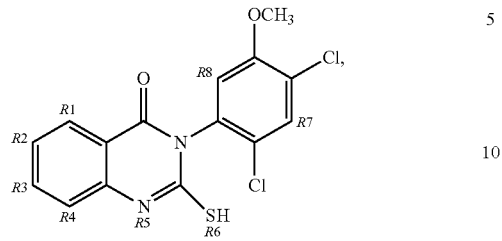

wherein each of R1 through R8 is selected from the group consisting of hydrogen, fluorine, chlorine, bromine, iodine, carboxyl, alkanes, cyclic alkanes, alkenes, cyclic alkenes, alkynes, ketones, aldehydes, carboxylic acids, ethers, esters amines, amides, monocyclic or polycyclic arene, heteroarenes, phenols, benzoic acid, membrane-targeting signal, and a mitochondria-targeting signal; and wherein at least one R-group comprises a targeting signal selected from the group consisting of palmitic acid, stearic acid, myristic acid, and oleic acid.

8. The method of claim 7, wherein the administering is performed at least one of prior to a cancer treatment, with a cancer treatment, and following a cancer treatment.

* * * * *